US007741432B2

(12) United States Patent
Parlati et al.

(10) Patent No.: US 7,741,432 B2
(45) Date of Patent: Jun. 22, 2010

(54) SUBSTRATE FOR RPN11 ENZYMATIC ACTIVITY

(75) Inventors: Francesco Parlati, San Francisco, CA (US); Monette Aujay, San Francisco, CA (US); Mark K. Bennett, Moraga, CA (US)

(73) Assignee: Proteolix, Inc., San Francisco, CA (US)

( * ) Notice: Subject to any disclaimer, the term of this patent is extended or adjusted under 35 U.S.C. 154(b) by 94 days.

(21) Appl. No.: 11/443,819

(22) Filed: May 30, 2006

(65) Prior Publication Data

US 2006/0280731 A1 Dec. 14, 2006

Related U.S. Application Data

(60) Provisional application No. 60/685,426, filed on May 27, 2005, provisional application No. 60/709,659, filed on Aug. 19, 2005.

(51) Int. Cl.
*C07K 14/00* (2006.01)

(52) U.S. Cl. .......................................... 530/300; 514/2

(58) Field of Classification Search ....................... None
See application file for complete search history.

(56) References Cited

U.S. PATENT DOCUMENTS

| | | | |
|---|---|---|---|
| 5,340,736 | A | 8/1994 | Goldberg |
| 2002/0156012 | A1 | 10/2002 | Lyapina et al. |
| 2003/0153097 | A1 | 8/2003 | Deshaies et al. |
| 2003/0166643 | A1 | 9/2003 | McDevitt et al. |

FOREIGN PATENT DOCUMENTS

| | | | |
|---|---|---|---|
| JP | 09000263 | A | 1/1997 |
| WO | WO-98/10779 | | 3/1998 |
| WO | WO-99/01567 | A | 1/1999 |
| WO | WO-02/055536 | A2 | 7/2002 |

OTHER PUBLICATIONS

Verma et al., "Role of Rpn11 Metalloprotease in Deubiquitination and Degradation by the 26S Proteasome", Science 298: 611-615 (2002).*

Guterman et al., "Complementary Roles for Rpn11 and Ubp6 in Deubiquitination and Proteolysis by the Proteasome," The Journal of Biological Chemistry, 279(3):1729-1738 (2004).

Lacombe et al., Further characterization of the putative human isopeptidase T catalytic site,: FEBS Letters, 531(3):469-474 (2002).

McCullough et al., "AMSH is an endosome-associated ubiquitin isopeptidase," The Journal of Cell Biology, 166(4):487-492 (2004).

Altschul et al., J. Mol. Biol. 215:403-410 (1990).

Altschul et al., Nuc. Acids Res. 25:3389-3402 (1997).

Carillo et al., SIAM J. Applied Math 48:1073-1082 (1988).

Ciechanover et al., Trends in Cell Biol. 14(3):103-106 (2004).

Ciechanover, Cell 79:13-21 (1994).

Cohen, Science 267:959-960 (1995).

Collins, T. Lab. Invest. 68:499-508 (1993).

Devereux et al., Nucleic Acids Research 12(1):387-395 (1984).

Eytan et al., JBC 268(7):4668-4674 (1993).

Garrett et al., J. Clin. Invest. 111:1771-1782 (2003).

Gonzales et al., Arch Med. Res. 28, Spec. No. 139-140 (1997).

Hardy et al., Trans. Genet. 8:55-61 (1992).

Harris et al., J. Bone Miner. Res. 9(6):855-863 (1994).

Hilvert, Chem.-Biol. 201-203 (1994).

Kojima et al., Fed. Eur. Biochem. Soc. 304:57-60 (1992).

Kumatori et al., Proc. Natl. Acad. Sci. USA 87:7071-7075 (1990).

Liu et al., Proc. Natl. Acad. Sci. USA 6584-6588 (1994).

Miranda et al., Proc. Natl. Acad. Sci, USA 1181-1186 (1999).

Muir et al., Proc. Natl. Acad. Sci USA 6705-6710 (1998).

Palombella et al., Cell 78:773-785 (1994).

Paugam et al., Trends Parasitol. 19(2):55-59 (2003).

Qureshi et al., J. Immuno. 171:1515-1525 (2003).

Thanos et al., Cell 80:529-532 (1995).

Traenckner et al., EMBO J. 13:5433-5441 (1994).

Verma et al., Mol. Biol. Cell 11:3425-3439 (2000).

Verma et al., Science 306:117-120 (2004).

Wallace, Curr. Opin. Biotechnol. 403-410 (1995).

Yao et al., Nature 419:403-407 (2002).

* cited by examiner

*Primary Examiner*—Anand U Desai
(74) *Attorney, Agent, or Firm*—Ropes & Gray LLP

(57) ABSTRACT

The present application provides peptides that serve as substrates for proteasome enzymatic activity, e.g., the enzymatic activity of Rpn11, a metalloprotease of the 19S regulatory particle. The present application also provides methods and compositions employing the peptide substrates.

28 Claims, 5 Drawing Sheets

SEQUENCE LISTING

<160> NUMBER OF SEQ ID NOS: 18

<210> SEQ ID NO 1
<211> LENGTH: 14
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 12, 13, 14
<223> OTHER INFORMATION: Xaa = S,C or A

<400> SEQUENCE: 1

Met Gln Ile Phe Val Lys Thr Leu Arg Ala Asn Xaa Xaa Xaa
 1               5                  10

-continued

<210> SEQ ID NO 2
<211> LENGTH: 685
<212> TYPE: PRT
<213> ORGANISM: Homo sapiens

<400> SEQUENCE: 2

```
Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
    370                 375                 380
```

-continued

Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
    530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
                565                 570                 575

Phe Ala Gly Lys Gln Leu Glu Asp Gly Arg Thr Leu Ser Asp Tyr Asn
            580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
    610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
                645                 650                 655

Gln Leu Glu Asp Gly Arg Thr Leu Ser Asp Tyr Asn Ile Gln Lys Glu
            660                 665                 670

Ser Thr Leu His Leu Val Leu Arg Leu Arg Gly Gly Val
        675                 680                 685

<210> SEQ ID NO 3
<211> LENGTH: 29
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 3

Met Gln Ile Phe Val Lys Thr Leu Arg Ala Asn Ser Ser Ser Val Xaa
 1               5                  10                  15

Lys Leu Ala Ala Ala Leu Tyr His His His His His His
            20                  25

-continued

<210> SEQ ID NO 4
<211> LENGTH: 29
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 4

Met Gln Ile Phe Val Lys Thr Leu Arg Ala Asn Ser Ser Cys Val Xaa
1 5 10 15

Lys Leu Ala Ala Ala Leu Tyr His His His His His His
20 25

<210> SEQ ID NO 5
<211> LENGTH: 29
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 5

Met Gln Ile Phe Val Lys Thr Leu Arg Ala Asn Ser Cys Ser Val Xaa
1 5 10 15

Lys Leu Ala Ala Ala Leu Tyr His His His His His His
20 25

<210> SEQ ID NO 6
<211> LENGTH: 29
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 6

Met Gln Ile Phe Val Lys Thr Leu Arg Ala Asn Cys Ser Ser Val Xaa
1 5 10 15

Lys Leu Ala Ala Ala Leu Tyr His His His His His His
20 25

<210> SEQ ID NO 7
<211> LENGTH: 29
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 7

Met Gln Ile Phe Val Lys Thr Leu Arg Ala Asn Cys Cys Cys Val Xaa
1 5 10 15

Lys Leu Ala Ala Ala Leu Tyr His His His His His His
20 25

-continued

```
<210> SEQ ID NO 8
<211> LENGTH: 28
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 8

Met Gln Ile Phe Val Lys Thr Leu Arg Ala Asn Ser Ser Ser Val Xaa
 1               5                  10                  15

Lys Leu Ala Ala Ala Leu Tyr His His His His His
            20                  25


<210> SEQ ID NO 9
<211> LENGTH: 26
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 9

Met Gln Ile Phe Val Lys Thr Leu Arg Ala Asn Ser Ser Ser Val Xaa
 1               5                  10                  15

Lys Leu Ala Ala Ala Leu Tyr His His His
            20                  25


<210> SEQ ID NO 10
<211> LENGTH: 24
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 10

Met Gln Ile Phe Val Lys Thr Leu Arg Ala Asn Ser Ser Ser Val Xaa
 1               5                  10                  15

Lys Leu Ala Ala Ala Leu Tyr His
            20


<210> SEQ ID NO 11
<211> LENGTH: 23
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 11

Met Gln Ile Phe Val Lys Thr Leu Arg Ala Asn Ser Ser Ser Val Xaa
 1               5                  10                  15

Lys Leu Ala Ala Ala Leu Tyr
            20
```

-continued

```
<210> SEQ ID NO 12
<211> LENGTH: 21
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 12

Met Gln Ile Phe Val Lys Thr Leu Arg Ala Asn Ser Ser Ser Val Xaa
 1               5                  10                  15

Lys Leu Ala Ala Ala
            20


<210> SEQ ID NO 13
<211> LENGTH: 18
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 13

Met Gln Ile Phe Val Lys Thr Leu Arg Ala Asn Ser Ser Ser Val Xaa
 1               5                  10                  15

Lys Leu


<210> SEQ ID NO 14
<211> LENGTH: 16
<212> TYPE: PRT
<213> ORGANISM: Artificial Sequence
<220> FEATURE:
<223> OTHER INFORMATION: peptide substrate
<220> FEATURE:
<221> NAME/KEY: VARIANT
<222> LOCATION: 16
<223> OTHER INFORMATION: Xaa = D or A

<400> SEQUENCE: 14

Met Gln Ile Phe Val Lys Thr Leu Arg Ala Asn Ser Ser Ser Val Xaa
 1               5                  10                  15


<210> SEQ ID NO 15
<211> LENGTH: 14
<212> TYPE: PRT
<213> ORGANISM: Artificial Sequence
<220> FEATURE:
<223> OTHER INFORMATION: peptide substrate

<400> SEQUENCE: 15

Met Gln Ile Phe Val Lys Thr Leu Arg Ala Asn Ser Ser Ser
 1               5                  10


<210> SEQ ID NO 16
<211> LENGTH: 310
<212> TYPE: PRT
<213> ORGANISM: Artificial Sequence
<220> FEATURE:
<223> OTHER INFORMATION: peptide substrate
```

-continued

<400> SEQUENCE: 16

Met Asp Arg Leu Leu Arg Leu Gly Gly Gly Met Pro Gly Leu Gly Gln
1 5 10 15

Gly Pro Pro Thr Asp Ala Pro Ala Val Asp Thr Ala Glu Gln Val Tyr
20 25 30

Ile Ser Ser Leu Ala Leu Leu Lys Met Leu Lys His Gly Arg Ala Gly
35 40 45

Val Pro Met Glu Val Met Gly Leu Met Leu Gly Glu Phe Val Asp Asp
50 55 60

Tyr Thr Val Arg Val Ile Asp Val Phe Ala Met Pro Gln Ser Gly Thr
65 70 75 80

Gly Val Ser Val Glu Ala Val Asp Pro Val Phe Gln Ala Lys Met Leu
85 90 95

Asp Met Leu Lys Gln Thr Gly Arg Pro Glu Met Val Val Gly Trp Tyr
100 105 110

His Ser His Pro Gly Phe Gly Cys Trp Leu Ser Gly Val Asp Ile Asn
115 120 125

Thr Gln Gln Ser Phe Glu Ala Leu Ser Glu Arg Ala Val Ala Val Val
130 135 140

Val Asp Pro Ile Gln Ser Val Lys Gly Lys Val Val Ile Asp Ala Phe
145 150 155 160

Arg Leu Ile Asn Ala Asn Met Met Val Leu Gly His Glu Pro Arg Gln
165 170 175

Thr Thr Ser Asn Leu Gly His Leu Asn Lys Pro Ser Ile Gln Ala Leu
180 185 190

Ile His Gly Leu Asn Arg His Tyr Tyr Ser Ile Thr Ile Asn Tyr Arg
195 200 205

Lys Asn Glu Leu Glu Gln Lys Met Leu Leu Asn Leu His Lys Lys Ser
210 215 220

Trp Met Glu Gly Leu Thr Leu Gln Asp Tyr Ser Glu His Cys Lys His
225 230 235 240

Asn Glu Ser Val Val Lys Glu Met Leu Glu Leu Ala Lys Asn Tyr Asn
245 250 255

Lys Ala Val Glu Glu Glu Asp Lys Met Thr Pro Glu Gln Leu Ala Ile
260 265 270

Lys Asn Val Gly Lys Gln Asp Pro Lys Arg His Leu Glu Glu His Val
275 280 285

Asp Val Leu Met Thr Ser Asn Ile Val Gln Cys Leu Ala Ala Met Leu
290 295 300

Asp Thr Val Val Phe Lys
305 310

<210> SEQ ID NO 17
<211> LENGTH: 13
<212> TYPE: PRT
<213> ORGANISM: Artificial Sequence
<220> FEATURE:
<221> NAME/KEY: VARIANT
<222> LOCATION: 11
<223> OTHER INFORMATION: Xaa = Any Amino Acid
<220> FEATURE:
<223> OTHER INFORMATION: peptide substrate

<400> SEQUENCE: 17

His Ser His Pro Gly Phe Cys Trp Leu Ser Xaa Val Asp
1 5 10

-continued

```
<210> SEQ ID NO 18
<211> LENGTH: 35
<212> TYPE: PRT
<213> ORGANISM: Artificial Sequence
<220> FEATURE:
<221> NAME/KEY: VARIANT
<222> LOCATION: 17
<223> OTHER INFORMATION: Xaa = Any Amino Acid
<220> FEATURE:
<223> OTHER INFORMATION: peptide substrate

<400> SEQUENCE: 18

Met Val Val Gly Trp Tyr His Ser His Pro Gly Phe Cys Trp Leu Ser
 1              5                   10                  15

Xaa Val Asp Ile Asn Thr Gln Gln Ser Phe Glu Ala Leu Ser Glu Arg
            20                  25                  30

Ala Val Ala
        35
```

SUBSTRATE FOR RPN11 ENZYMATIC ACTIVITY

CROSS REFERENCE TO RELATED APPLICATIONS

This application claims priority to and the benefit of the filing dates of U.S. Provisional Application Ser. Nos. 60/709,659 and 60/685,426, filed on Aug. 19, 2005 and May 27, 2005, respectively, the contents of which are hereby incorporated by reference in their entirety.

BACKGROUND

Proteolysis by the 26S proteasome proceeds by binding ubiquitinated substrate protein to the 19S regulatory particle, followed by its deubiquitination, unfolding and translocation into the lumen of the 20S core, where it is degraded. In recent years, it has become evident that the proteasome is an appealing target for therapeutic intervention in cancer, immune-related disorders, inflammation, ischemic conditions, neurodegenerative disorders and other diseases. To date, the only FDA-approved proteasome inhibitor (VELCADE™) works by inhibiting the activity of the 20S core peptidases. Nonetheless, inhibiting other enzymatic activities residing within the proteasome complex could serve as equally effective, if not better, means of controlling proteasome function.

One such target candidate is the metalloprotease, Rpn11, residing within the 19S regulatory particle. It is responsible for the initial deubiquitination of target proteins (Eytan, et al. JBC 268(7):4668-4674 (1993); Verma, et al. Science 298: 611-615 (2002)). The human homolog of this yeast protein is POH1. To date, a recombinant form of Rpn11 has not been generated. However, the deubiquitinating activity associated with Rpn11 can be distinguished in the context of a purified 26S proteasome complex by its sensitivity to ATP-γS and 1,10-phenanthroline (OPA) and insensitivity to 20S core protease inhibitors and the classic DUB inhibitors (ubiquitin aldehyde (UB-Al) or ubiquitin vinylsulphone (UbVS)).

In the pursuit to learn more about Rpn11 and its deubiquitinating activity, several assays have been employed. Most utilize purified 26S proteasome extracts as the source of enzyme and look for degradation in the presence or absence of a DUB inhibitor. Detecting Rpn11 activity required a ubiquitinated protein such as Ub-sic 1 (Verma et al., supra) and the reaction was monitored by SDS-PAGE followed by immunoblotting with either α-ubiquitin (α-Ub) or α-protein such as α-sic 1. Substrates that were radio- or fluorescent-labeled still required a step that separated uncleaved substrate from cleaved product such as PAGE (Eytan et al., supra) or TCA-precipitation (Yao et al., Nature 419: 403-407 (2002)), respectively.

Thus, a high throughput (HTP) assay employing novel Rpn11 substrate proteins is highly desirable in order to screen large numbers of molecules to identify modulators of Rpn11 activity.

BRIEF DESCRIPTION OF THE APPLICATION

Accordingly, this application provides peptides that are substrates of proteasome enzymatic (e.g., Rpn11) activity, and various compositions and methods employing the peptide substrates, such as assays measuring proteasome (e.g., Rpn11) enzymatic activities or screening for agents that modulate proteasome enzymatic activities. The terms "peptide," "polypeptide," and "proteins" are used interchangeably herein. The term "proteasome" means the 26S proteasome, the 19S regulatory particle, a protein complex comprising the 19S regulatory particle, or other protein complexes or components comprising an Rpn11 or an Rpn11-like protein involved in ubiquitin-mediated proteolysis. The term "Rpn11" is also used interchangeably with "POH1" herein, and refers to any polypeptide that confers an Rpn11 enzymatic activity, for example, the deubiquitination activity.

A first aspect of the application provides a peptide substrate for a protease of the 26S proteasome, the 20S proteasome, or the 19S regulatory particle. In certain embodiments, the peptide substrate comprises an amino acid sequence at least 50%, 60%, 70%, 80%, 90%, 95%, or 100% identical to SEQ ID NO:1 and a ubiquitin moiety that is at least 70%, 80%, 90%, 95%, or 100% identical to the first 76-amino acid sequence of SEQ ID No:2. In certain embodiments, the peptide substrate comprises a ubiquitin moiety that is at least 70%, 80%, 90%, 95%, or 100% identical to the first 76-amino acid sequence of SEQ ID No:2, a first amino acid sequence at least 50%, 60%, 70%, 80%, 90%, 95%, or 100% identical to SEQ ID NO:1 and an additional amino acid sequence, preferably beginning at the C-terminus of the first amino acid sequence, having at least 3, 5, 8, 10, 12, 15, 18, 20, 25, 30, 40, 50, 75, 100, 200, 300, 500 or more amino acids. In certain embodiments, the peptide substrate comprises an amino acid sequence at least 50%, 60%, 70%, 80%, 90%, 95%, or 100% identical to any of SEQ ID NO:3-15 and a ubiquitin moiety that is at least 70%, 80%, 90%, 95%, or 100% identical to the first 76-amino acid sequence of SEQ ID No:2.

In certain embodiments, the peptide substrate further comprises one or more ubiquitin moieties, e.g., at the N-terminus of the peptide. In certain embodiments, one or more ubiquitin moieties may be linked to the peptide through the K(s) of the peptide.

In certain embodiments, a ubiquitin moiety comprises an amino acid sequence that is 50%, 60%, 70%, 80%, 90%, or 100% identical to the first 76-amino acid sequence of SEQ ID NO:2. The 76-amino acid ubiquitin repeat unit of SEQ ID NO:2 is also referred to as Ub herein. In certain embodiments, a ubiquitin moiety comprises 1, 2, 3, 4, 5, 6, 7, 8, 9, 10, 15, 20, 25, 30, 40, 50, 100 or more repeats of Ub. In certain embodiments, a ubiquitin moiety comprises one or more Ub repeats, except that the 75th amino acid of at least one Ub repeat is A. In certain embodiments, a ubiquitin moiety comprises one or more Ub repeats, except that the 76th amino acid of at least one Ub repeat is A. In certain embodiments where a ubiquitin moiety comprises one or more Ub repeats, the 76th amino acid of at least one Ub repeat is G or A.

In certain embodiments, the peptide substrate further comprises a detectable agent linked to the peptide. The detectable agent can be linked to the peptide using different methods, which may depend on the identity of the detectable agent and/or the part of the peptide to be linked with the detectable agent. For example, the detectable agent may be linked to the peptide via C residue(s) of the peptide. The detectable agent can be a fluorescent label, which can be linked to the peptide substrate by noncovalent or covalent linkage. A fluorescent label may comprise a fluorescent peptide that can be linked to the peptide by noncovalent or covalent linkage, for example, a peptide bond. Alternatively, the detectable agent can be a radioactive label, for example, a radio-labeled amino acid such as an $^{35}$S-C or $^{35}$S-M.

In other embodiments, the peptide substrate may comprise a target portion, e.g., an N-terminal or C-terminal portion, that specifically binds to a selection agent. The selection agent can be an antibody, which recognizes the target portion of the peptide substrate. Alternatively, the selection agent can be a divalent metal ion, which specifically interacts or associates with the target portion of the peptide substrate.

Another aspect of the application provides nucleic acids encoding the various proteins and peptide substrates described herein.

Another aspect of the application provides methods employing a peptide substrate of the application.

Certain embodiments provide a method for selecting an agent that modulates proteasome activity, e.g., enzymatic activity of the 26S proteasome or the 19S regulatory particle. The method may include providing a peptide substrate of the application, for example, a peptide substrate comprising an amino acid sequence of SEQ ID NO:1 and one or more ubiquitin moieties, and combining the peptide with a reaction mixture suitable for measuring proteasome activity in the presence of a test agent. A change in the proteasome activity in the presence of the test agent as compared to the proteasome activity in the absence of the test agent indicates that the test agent modulates the proteasome activity. The proteasome activity can be determined by, for example, measuring the level of cleavage of the ubiquitin moiety(s) from the peptide. The level of cleavage may be indicated by the rate and/or extent of cleavage. The method is useful for selecting an agent that enhances or inhibits the proteasome activity.

Certain embodiments provide a method for selecting a proteasome inhibitor agent. The proteasome inhibitor agent may comprise a ubistatin-like molecule or moiety or a ubiquitin-binding molecule or moiety. The proteasome inhibitor agent that binds ubiquitin may inhibit the substrate from being proteolyzed or may inhibit proteasome activity through other mechanisms. The inhibitor agent may or may not have intrinsic fluorescence.

The method may include providing a peptide substrate of the application that has a fluorescent label, e.g., a peptide substrate comprising an amino acid sequence of SEQ ID NO:1, one or more ubiquitin moieties, and a fluorescent label, and determining the fluorescence polarization of the peptide substrate in the presence as compared to the absence of a test agent. A difference in the fluorescence polarization in the presence of the test agent versus in the absence of the test agent indicates that the test agent may be a proteasome inhibitor agent.

Alternatively, the method may include providing a peptide substrate of the application in a suitable reaction mixture in the presence or absence of a test agent and determining whether there is any difference in the molecular weight and/or size of the peptide substrate in the presence as compared to the absence of the test agent. A ubistatin-like molecule can cause aggregation or multimerization of ubiquitin moieties attached to a peptide, and therefore, an increased molecular weight and/or size of the peptide substrate in the presence as compared to the absence of the test agent indicates that the test agent may be a ubistatin-like molecule. Molecular weight and/or size can be determined by various methods, such as native gel electrophoresis, size-exclusion chromatography, light scattering, etc.

The method may include providing a peptide substrate of the application, e.g., a peptide substrate comprising an amino acid sequence of SEQ ID NO:1 and one or more ubiquitin moieties, and determining whether the intrinsic fluorescence of a test agent changes when the test agent is combined with the peptide substrate in a suitable reaction mixture. A change in the intrinsic fluorescence of the test agent in the presence of the peptide substrate indicates that the test agent may be a proteasome inhibitor.

In other embodiments, a method for selecting a proteasome inhibitor agent may employ a reaction mixture that comprises a ubistatin molecule (e.g., ubistatin A or B), in addition to a peptide substrate of the application and with or without a test inhibitor agent. A change in the intrinsic fluorescence of the ubistatin molecule (e.g., ubistatin A or B) measured in the presence of the test inhibitor agent as compared to the absence of the test inhibitor agent indicates that the test inhibitor agent is a ubistatin-like proteasome inhibitor. The test inhibitor agent itself may or may not have intrinsic fluorescence. This method can be particularly useful for selecting a ubistatin-like proteasome inhibitor that can compete against ubistatin for binding with ubiquitin moieties.

A further aspect of the application provides a method for selecting an agent that modulates activity of various components of proteasome or various stages of the ubiquitin-mediated proteolysis process. The various components of proteasome and various stages of the ubiquitin-mediated proteolysis may include entry into the proteasome of ubiquitinated proteins; deubiquitination of the proteins, e.g., by Rpn11; unfolding of the proteins, e.g., ATPases Associated with various cellular Activities (AAA ATPase); degradation of the deubiquitinated proteins by a core peptidase.

The method may employ at least two peptide substrates, for example, a first peptide substrate comprising a ubiquitinated-peptide and a first fluorescent label, and a second peptide substrate comprising a non-ubiquitinated peptide and a second fluorescent label, wherein the first and second fluorescent labels are detectable at different wavelengths. A ubiquitinated-peptide may comprise an amino acid sequence of SEQ ID NO:1 and one or more ubiquitin moieties. A non-ubiquitinated peptide may be any peptide that can serve as a substrate for a core peptidase, e.g., a chymotryptic-like protease, a tryptic-like protease, or a PGPH (or caspase)-like protease. The method may also include measuring the fluorescence at the first label detectable wavelength in the presence of a 26S proteasome and in the presence and absence of a test agent, and optionally also measuring the fluorescence at the second label detectable wavelength in the presence of the 26S proteasome and in the presence and absence of a test agent. A change in fluorescence of the first peptide substrate in the presence of the test agent as compared to the fluorescence in the absence of the test agent indicates that the test agent modulates an activity associated with the 19S regulatory particle. A change in fluorescence of the second peptide substrate in the presence of the test agent as compared to the fluorescence in the absence of the test agent indicates that the test agent modulates a 20S core peptidase.

Another aspect of the application provides methods and compositions employing an agent selected according to a method of the application. For example, certain embodiments provide a method for treating or preventing in a subject a condition associated with aberrant ubiquitin-mediated proteolysis or proteasome activity comprising administering to the subject a composition comprising an agent that modulates the proteasome activity, particularly an enzymatic activity associated with the 19S regulatory particle. An example of the enzymatic activity associated with the 19S regulatory particle is the Rpn11 enzymatic activity.

BRIEF DESCRIPTION OF THE DRAWINGS

FIG. 1 further shows that proteolysis of the substrate Ub4-peptide (29) and Ub4-peptide-C14(29) by the 26S proteasome is inhibited by o-phenanthroline and ATPγS but not ubiquitin aldehyde. 2 μg of Ub4-peptide(29) or Ub4-peptide-C14(29) were incubated with 60 nM 26S proteasome in buffer B [50 mM Tris pH 8.0; 10 mM $MgCl_2$; 1 mM DTT; 1 mM ATP] and where indicated 5 mM ATPγS, 1 mM O-phenanthroline (OPA) and 5 μM ubiquitin aldehyde (Ub-aldehyde) in a volume of 20 μl for 2 hours at 37° C. Reactions were stopped by adding 7.5 μl loading dye and boiled at 100° C. for 5 minutes. Reactions were then loaded on an SDS-PAGE gel, reaction products were separated by electrophoresis and bands were visualized with brilliant blue.

FIG. 2 further shows that proteolysis of the substrate Ub4-peptide-C14(14) is inhibited by o-phenanthroline and ATPγS using 26S proteasome from source A but not Source B. Reactions were performed as described above for FIG. 1 except for the following modifications: 2 μg of Ub4-peptide-C14(14) was incubated with 60 nM of 26S from either source A or source B.

FIG. 3 shows that cleavage of the peptide-C14(29) coupled to fluorescein from Ub4-peptide-C14 (29) coupled to fluorescein results in a decrease in the fluorescence polarization signal.

DETAILED DESCRIPTION OF THE APPLICATION

Figure 1:
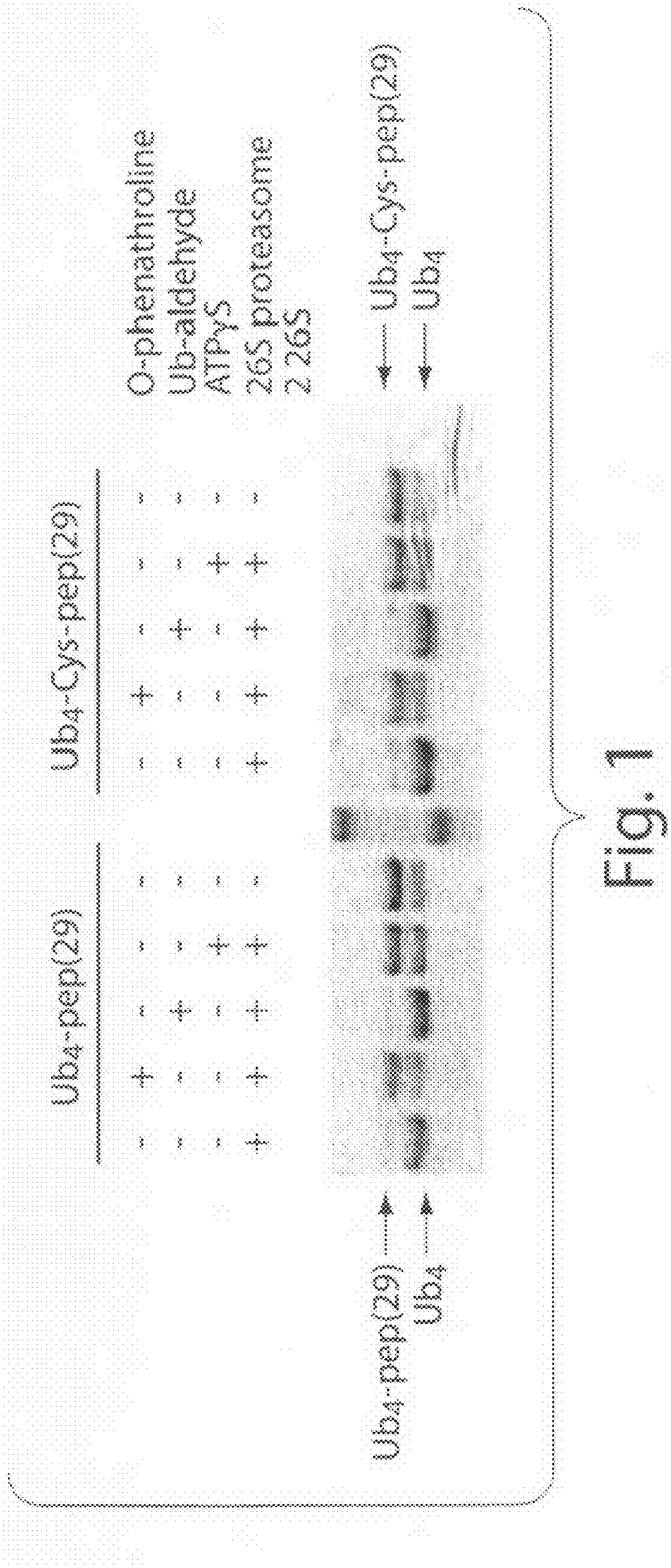
FIG. 1 shows that changing S14 of the peptide comprising the sequence of SEQ ID NO:3 to C14 (SEQ ID NO:4) does not alter the substrate's ability to be recognized and cleaved by Rpn11. Each peptide substrate further comprises an N-terminal ubiquitin moiety that has 4 Ub repeats (Ub4).
Figure 2:
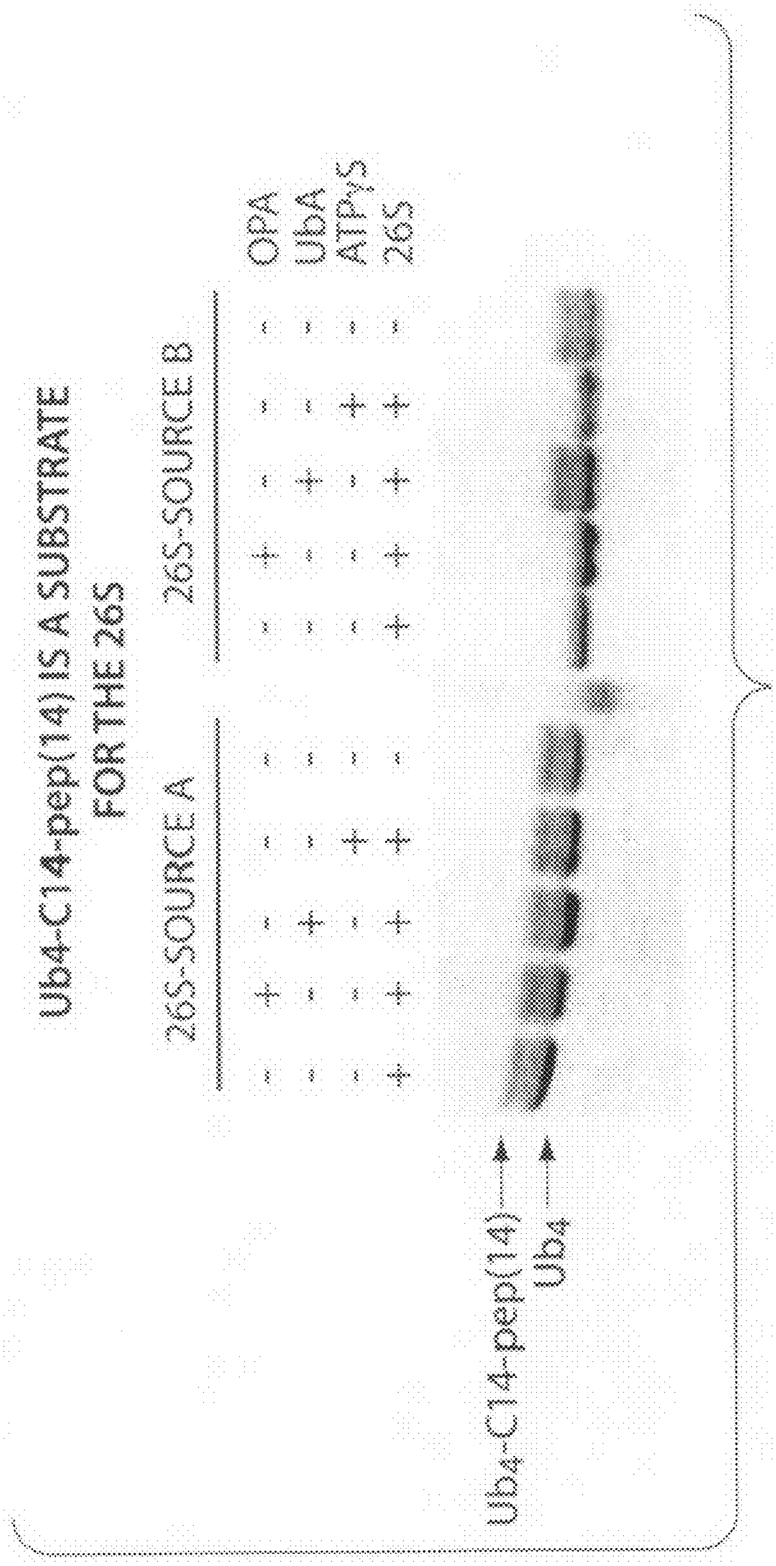
FIG. 2 shows that changing S14 of the peptide comprising the sequence of SEQ ID NO:15 to C14 does not alter the substrate's ability to be recognized and cleaved by Rpn11. Each peptide substrate further comprises an N-terminal ubiquitin moiety that has 4 Ub repeats (Ub4).
Figure 3:
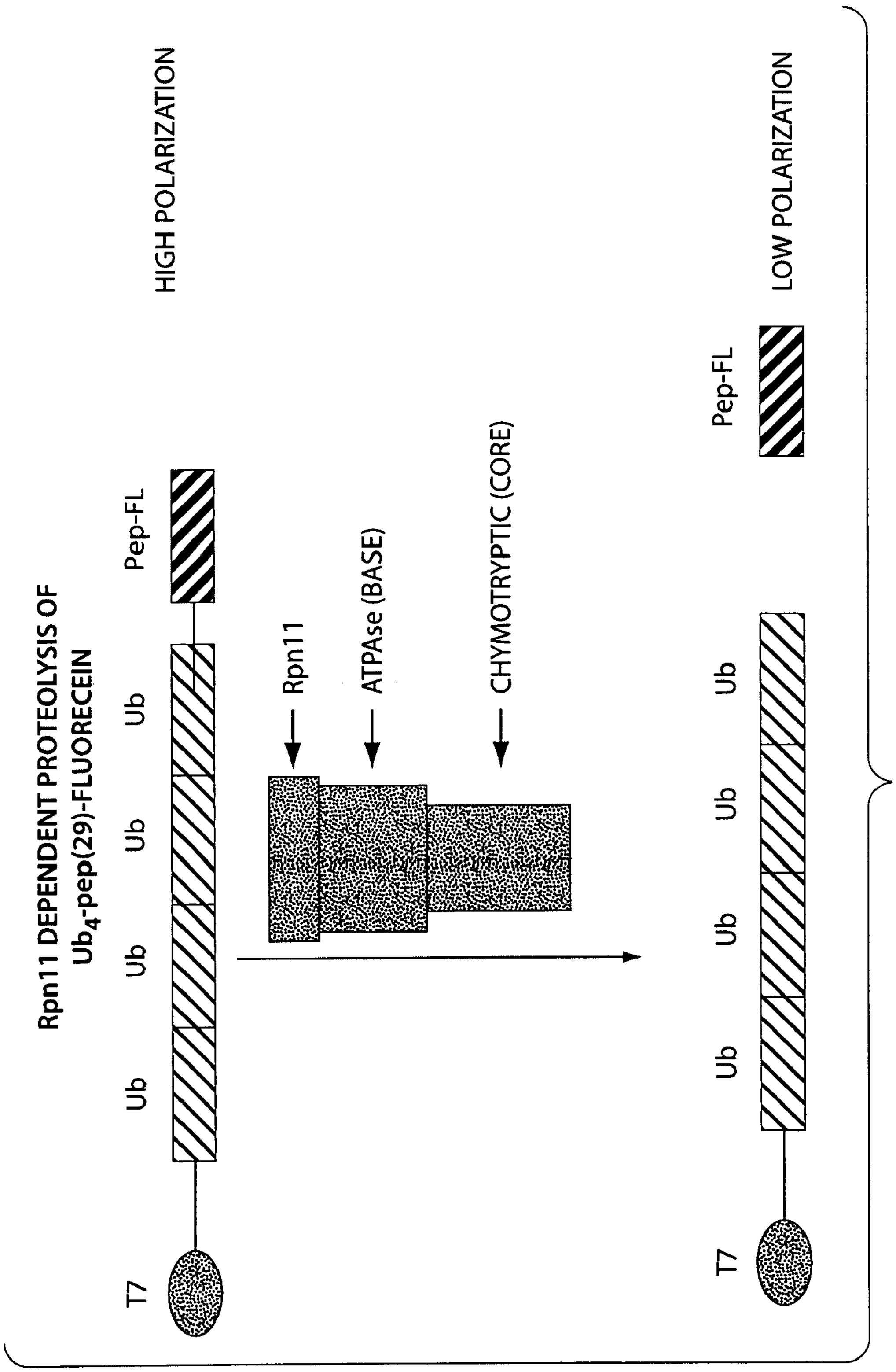
FIG. 3 is a schematic representation of a fluorescence polarization (FP) assay using an illustrative peptide substrate of the application that comprises a fluorescent label, for example fluorescein.
Figure 4:
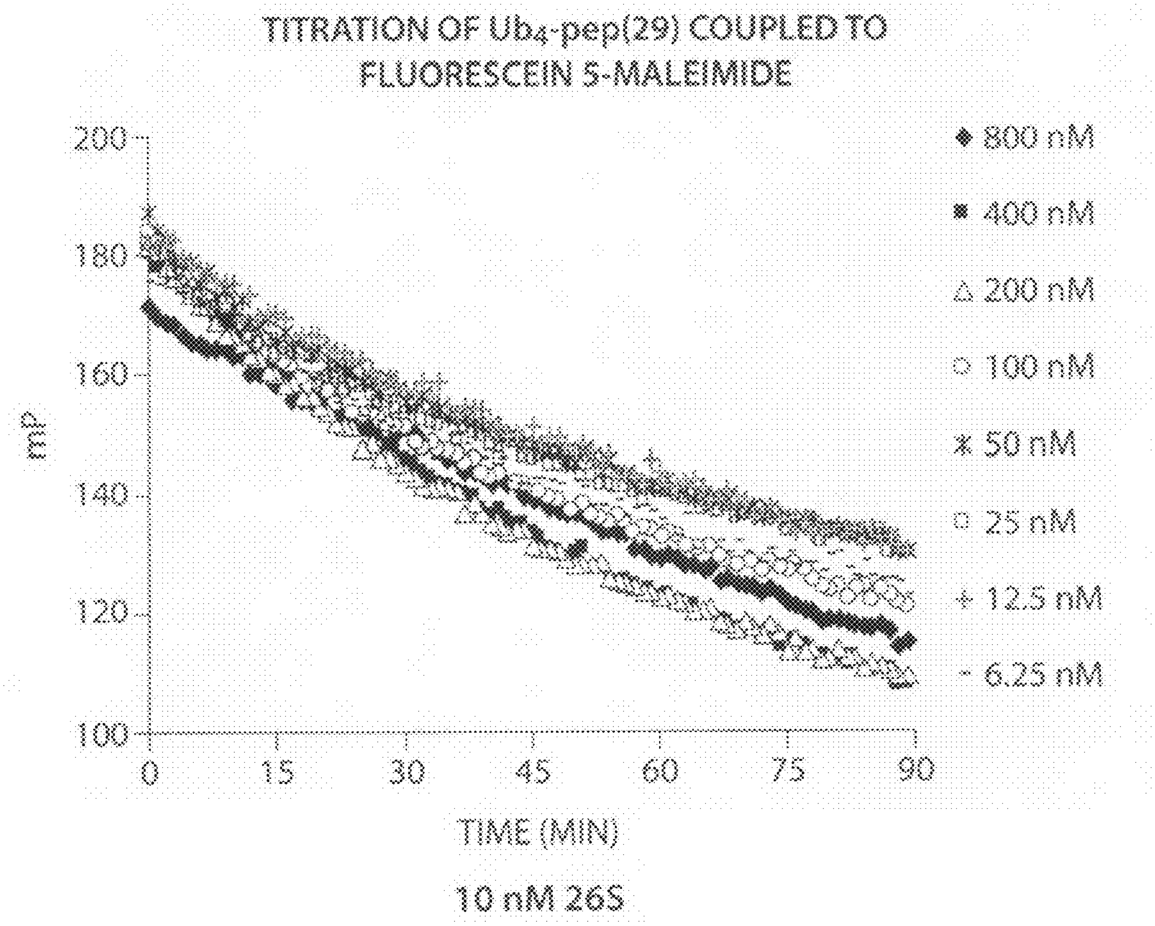
FIG. 4 shows the result of an FP assay using a peptide substrate of the application and kinetics of Ub4-peptide(29)-fluorescein proteolysis by the 26S proteasome. Various concentrations (as indicated) of Ub4-peptide(29) coupled to Fluorescein-5-maleimide was incubated with 10 nM 26S proteasome in 50 mM Tris pH 8.0; 10 mM $MgCl_2$; 1 mM DTT; 1 mM ATP at 28° C., and the liberation of peptide(29)-fluorescein was measured by fluorescence polarization (excitation at 485 nm; emission at 510 nm).
Figure 5A:
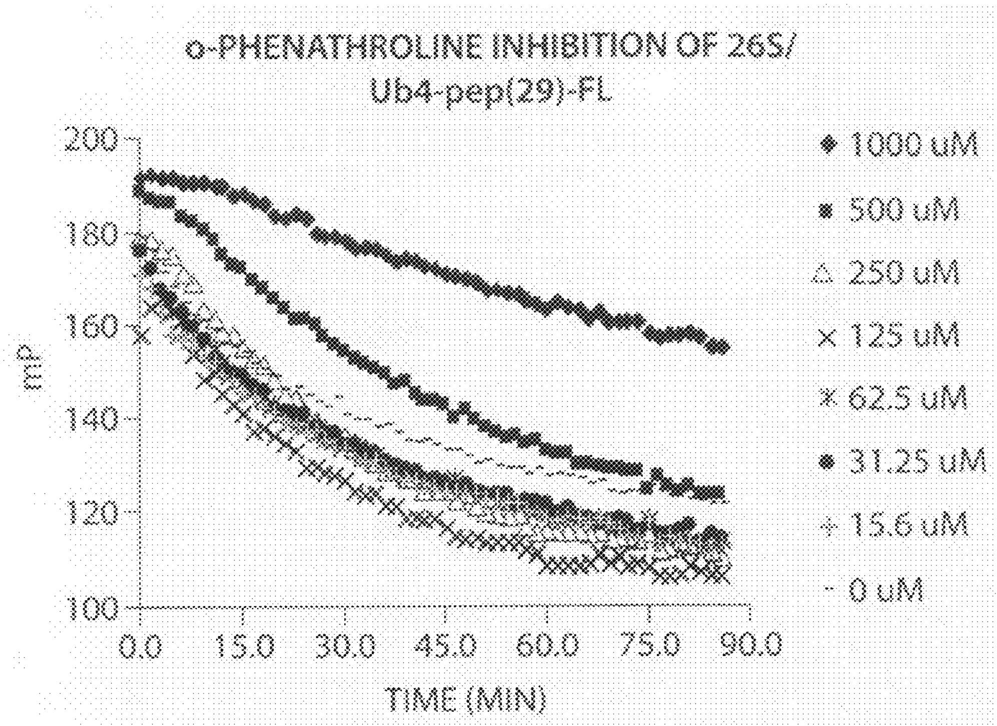
FIG. 5A illustrates a high throughput (HTP) FP assay that detects O-phenanthroline inhibition of Rpn11 activity. The results show that O-phenanthroline affects the kinetics of Ub4-peptide(29)-fluorescein proteolysis by the 26S proteasome. 100 nM Ub4-peptide coupled to fluorescein-5-maleimide was incubated with 10 nM 26S proteasome in 50 mM Tris pH 8.0; 10 mM $MgCl_2$; 1 mM DTT; 1 mM ATP at 28° C. and the liberation of peptide was measured by fluorescence polarization (excitation at 485 nm; emission at 510 nm) in the presence of various concentrations of o-phenanthroline (as indicated).
Figure 5B:
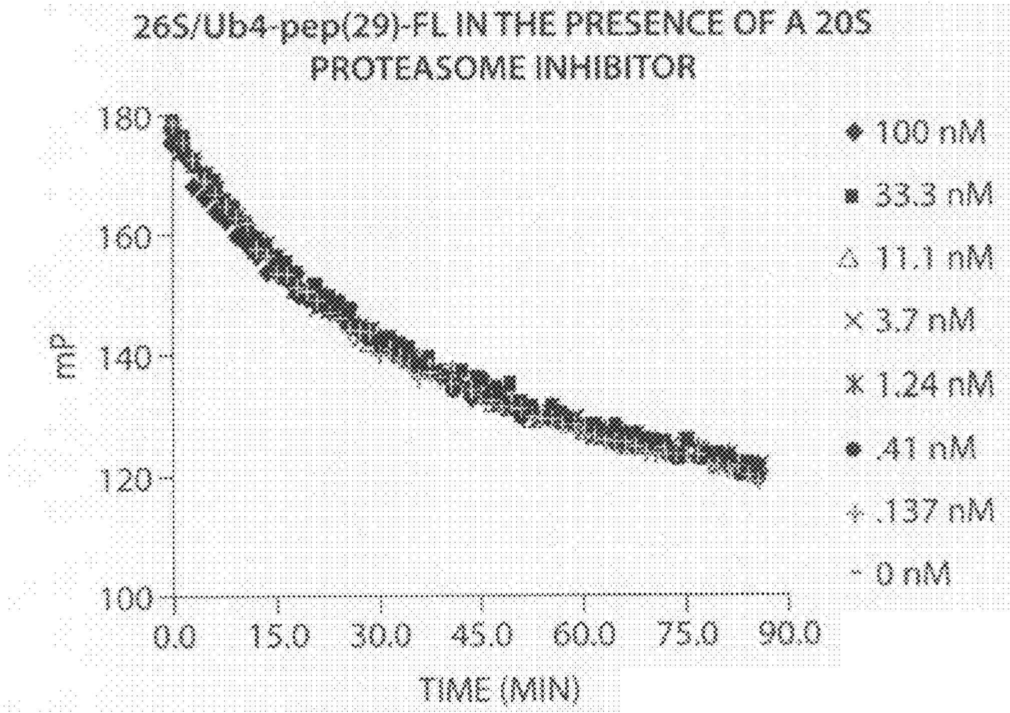
FIG. 5B illustrates that Rpn11 enzymatic activity is unaffected by the presence of a 20S proteasome inhibitor in the HTP FP assay using a peptide substrate of the application. The results show that the 20S proteasome inhibitor does not affect the kinetics of Ub4-peptide(29)-fluorescein proteolysis by the 26S proteasome. 100 nM Ub4-peptide coupled to fluorescein-5-maleimide was incubated with 10 nM 26S proteasome in 50 mM Tris pH 8.0; 10M $MgCl_2$; 1 mM DTT; 1 mM ATP at 28° C. and the liberation of peptide was measured by fluorescence polarization (excitation at 485 nm; emission at 510 nm) in the presence of various concentrations of 20S proteasome inhibitor (as indicated).

The major route for protein degradation in the nucleus and cytoplasm of eukaryotic cells is via the ubiquitin/26S proteasome pathway. The 26S proteasome comprises two major subparticles: the 20S proteasome and the 19S regulatory particle. The 20S proteasome is a cylindrical structure with an internal cavity that contains the peptidase active sites. Substrates of the proteasome are inserted into the cylinder, where they are susceptible to digestion by the peptidase active sites of the 20S proteasome. Entry into the 20S proteasome cylinder is governed by the 19S regulatory particle, which caps the ends of the 20S cylinder.

The 19S regulatory particle binds ubiquitinated substrates and translocates them into the inner cavity of the 20S cylinder, where they are degraded. The 19S regulatory particle can be further subdivided into two multiprotein complexes: the base and the lid. The base comprises a set of six ATPases that are thought to unfold substrates and translocate them into the 20S proteasome. The lid is comprised of a set of eight proteins, some of which have known functions, e.g., Rpn11. Biochemical data also indicate that the presence of the lid renders the proteasome selective for degrading ubiquitinated proteins.

The lid subcomplex of the 26S proteasome is evolutionarily related to the COP9-signalosome complex, but the significance of this similarity has remained unknown. There are reports in the literature that 26S proteasome preparations contain a variety of associated ubiquitin isopeptidase activities (Eytan et al., supra; Verma, et al., Mol Biol Cell 11:3425 (2000)). A more recent report (Verma et al., Science 298:611-615 (2002)) demonstrated that an ubiquitinated substrate can be completely deubiquitinated by purified 26S proteasome to yield unmodified substrate in the presence of a 20S proteasome inhibitor, e.g., VELCADE™.

Proteins that are destined for degradation by the ubiquitin/26S pathway are marked by the attachment of a multiubiquitin or polyubiquitin chain to the side chains of lysine residues on the target protein. Recent studies also show that N-terminal ubiquitination is also an important novel mode of protein modification and targets the protein for proteolysis by the 26S proteasome (Ciechanover and Ben-Saadon, Trends in Cell Biol. 14(3): 103-106 (2004)). The ubiquitinated protein is then recognized by the 26S proteasome by a mechanism that remains poorly understood. Subsequently the ubiquitinated protein is disengaged from any tightly bound partners, deubiquitinated, unfolded, and translocated into the central cavity of the 20S complex, where it is exhaustively degraded by the proteolytic active sites that are present in this inner cavity (core peptidase).

Rpn11, a metalloisopeptidase or metalloprotease and intrinsic subunit of the lid subcomplex of the 19S regulatory particle, contains a conserved, predicted metalloprotease motif (JAMM) that is critical for cell viability. For the purpose of this application, Rpn11 and POH1 are interchangeable. Rpn11, by mediating or catalyzing protein substrate deubiquitination is believed to define a key step in protein degradation by 26S proteasome (Verma et al., 2002, supra). Rpn11 and its orthologs are described in U.S. Patent Application Publication No. 20030166243. Accordingly, peptide substrates for Rpn11 are useful in studying Rpn11 activity and identifying agents that modulate Rpn11 activity, and thereby modulating ubiquitin-mediated proteolysis.

A representative amino acid sequence of an Rpn11 is set forth as follows:

```
gi|51701716|sp|O00487|PSDE_HUMAN
26S proteasome non-ATPase regulatory subunit 14
(26S proteasome regulatory subunit rpn11) (26S
proteasome-associated PAD1 homolog 1)
                                        (SEQ ID NO:16)
Met Asp Arg Leu Leu Arg Leu Gly Gly Gly Met Pro Gly

Leu Gly Gln Gly Pro Pro Thr Asp Ala Pro Ala Val Asp

Thr Ala Glu Gln Val Tyr Ile Ser Ser Leu Ala Leu Leu
```

-continued

Lys Met Leu Lys His Gly Arg Ala Gly Val Pro Met Glu

Val Met Gly Leu Met Leu Gly Glu Phe Val Asp Asp Tyr

Thr Val Arg Val Ile Asp Val Phe Ala Met Pro Gln Ser

Gly Thr Gly Val Ser Val Glu Ala Val Asp Pro Val Phe

Gln Ala Lys Met Leu Asp Met Leu Lys Gln Thr Gly Arg

Pro Glu Met Val Val Gly Trp Tyr His Ser His Pro Gly

Phe Gly Cys Trp Leu Ser Gly Val Asp Ile Asn Thr Gln

Gln Ser Phe Glu Ala Leu Ser Glu Arg Ala Val Ala Val

Val Val Asp Pro Ile Gln Ser Val Lys Gly Lys Val Val

Ile Asp Ala Phe Arg Leu Ile Asn Ala Asn Met Met Val

Leu Gly His Glu Pro Arg Gln Thr Thr Ser Asn Leu Gly

His Leu Asn Lys Pro Ser Ile Gln Ala Leu Ile His Gly

Leu Asn Arg His Tyr Tyr Ser Ile Thr Ile Asn Tyr Arg

Lys Asn Glu Leu Glu Gln Lys Met Leu Leu Asn Leu His

Lys Lys Ser Trp Met Glu Gly Leu Thr Leu Gln Asp Tyr

Ser Glu His Cys Lys His Asn Glu Ser Val Val Lys Glu

Met Leu Glu Leu Ala Lys Asn Tyr Asn Lys Ala Val Glu

Glu Glu Asp Lys Met Thr Pro Glu Gln Leu Ala Ile Lys

Asn Val Gly Lys Gln Asp Pro Lys Arg His Leu Glu Glu

His Val Asp Val Leu Met Thr Ser Asn Ile Val Gln Cys

Leu Ala Ala Met Leu Asp Thr Val Val Phe Lys

In certain embodiments, an Rpn11 of the present invention comprises an amino acid sequence that is at least 60%, 65%, 70%, 75%, 80%, 85%, 90%, 95%, 98%, 99%, or 100% identical to the amino acid sequence of SEQ ID NO:16. In certain embodiments, an Rpn11 of the present invention comprises an amino acid sequence that has amino acid substitutions, deletions, or additions at 1, 2, 3, 4, 5, 6, 7, 8, 9, or 10 positions of SEQ ID NO:16. In certain embodiments, such amino acid substitutions are conservative amino acid substitutions.

As reported by Verma et al., supra, a JAMM motif is required for an Rpn11 's ability to deubiquitinate and degrade Ub-Sic1. Mutation of the predicted active-site histidines to alanine (rpn11AXA) was lethal and stabilized ubiquitin pathway substrates in yeast. A JAMM motif can represented by the following amino acid sequence:

(SEQ ID NO:17)

His Ser His Pro Gly Phe Cys Trp Leu Ser Xaa Val Asp where Xaa is Ser or Gly, preferably Gly.

Alternatively, a JAMM motif may be characterized by the following sequence:

(SEQ ID NO:18)

Met Val Val Gly Trp Tyr His Ser His Pro Gly Phe Cys

Trp Leu Ser Xaa Val Asp Ile Asn Thr Gln Gln Ser Phe

Glu Ala Leu Ser Glu Arg Ala Val Ala where Xaa is Ser or Gly, preferably Gly; Ile is Val or Ile, preferably Ile; Gln is Lys or Gln, preferably Gln; Ala is Gln or Ala, preferably Ala; Ser is Asn, Thr or Ser, preferably Ser; and Glu is Ser, Pro, Asp or Glu, preferably Glu.

In certain embodiments, an Rpn11 of the present invention comprises a JAMM motif that is at least 70%, 75%, 80%, 85%, 90%, 95%, 98%, 99%, or 100% identical to the amino acid sequence of SEQ ID NO:17. In certain embodiments, an Rpn11 of the present invention comprises a JAMM motif that has amino acid substitutions, deletions, or additions at 1, 2, 3, 4 or 5 positions of SEQ ID NO:17. In certain embodiments, such amino acid substitutions are conservative amino acid substitutions. In specific embodiments, an Rpn11 of the present invention comprise a JAMM motif that is at least 70%, 75%, 80%, 85%, 90%, 95%, 98%, 99%, or 100% identical to the amino acid sequence of SEQ ID NO:18. In specific embodiments, an Rpn11 of the present invention comprises a JAMM motif that has amino acid substitutions, deletions, or additions at 1, 2, 3, 4, 5, 8, 10, 12, or 15 positions of SEQ ID NO:18. In certain embodiments, such amino acid substitutions are conservative amino acid substitutions.

In certain embodiments, an Rpn11 of the present invention comprises an amino acid sequence that is at least 60%, 65%, 70%, 75%, 80%, 85%, 90%, 95%, 98%, 99%, or 100 identical to the amino acid sequence of SEQ ID NO:16, and the Rpn11 protein comprises a JAMM motif that is at least 80%, 85%, 90%, 95%, 98%, 99%, or 100% identical to the amino acid sequence of SEQ ID NO:17.

In certain embodiments, an Rpn11 of the present invention comprises an amino acid sequence that is at least 60%, 65%, 70%, 75%, 80%, 85%, 90%, 95%, 98%, 99%, or 100 identical to the amino acid sequence of SEQ ID NO:16, and the Rpn11 protein comprises a JAMM motif that is at least 70%, 75%, 80%, 85%, 90%, 95%, 98%, 99%, or 100% identical to the amino acid sequence of SEQ ID NO:18.

In certain embodiments, an Rpn11 of the present invention comprises an amino acid sequence that has amino acid substitutions, deletions, or additions at 1, 2, 3, 4, 5, 6, 7, 8, 9, or 10 positions of SEQ ID NO:16, and the Rpn11 comprises a JAMM motif that has amino acid substitutions, deletions, or additions at 1, 2, 3, 4 or 5 positions of SEQ ID NO:17.

In certain embodiments, an Rpn11 of the present invention comprises an amino acid sequence that has amino acid substitutions, deletions, or additions at 1, 2, 5, 10, 15, 20, 30, 50, 60, 75, or 90 positions of SEQ ID NO:16, and the Rpn11 protein comprises a JAMM motif that has amino acid substitutions, deletions, or additions at 1, 2, 3, 4, 5, 8, 10, 12, or 15 positions of SEQ ID NO:18.

As used herein, "sequence identity" (or "% identical") means the percentage of identical amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988, Biocomputing: Informatics and Genome Projects, Smith, D. W., ed., Academic Press, New York, 1993, Computer Analysis of Sequence Data, Part I, Griffin, A. M., and Griffin, H. G., eds., Humana Press, New Jersey, 1994, Sequence Analysis in Molecular Biology, von Heinje, G., Academic Press, 1987, and Sequence Analysis Primer, Gribskov, M. and Devereux, J., eds., M Stockton Press, New York, 1991, and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894, Altschul, S., et al., J. Mol. Biol. 215: 403-410 (1990). The well known Smith-Waterman algorithm may also be used to determine sequence identity.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:

(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

Illustrative Peptides of the Application

One aspect of the present application provides various peptides or proteins, which may comprise any one of sequences of SEQ ID NOs:1-15 below. In certain embodiments, a peptide substrate for proteasome enzymatic (e.g., Rpn11) activity comprises an amino acid sequence of any of SEQ ID NOs:1 and 3-15 and further comprises a ubiquitin moiety. By "ubiquitin moiety" is meant a single, 76-amino acid ubiquitin moiety (Ub) or a polyubiquitin moiety, such as the 9-repeat polyubiquitin (as represented by the first 684 amino acids of SEQ ID NO:2) (also termed Ub9), or n repeats of Ub (also termed Ubn, wherein n can be any integral number). In preferred embodiments, the ubiquitin moiety is at the N-terminus of the peptide substrate, thus the peptide substrate is considered as being modified by N-terminal ubiquitination or N-terminal polyubiquitination. Alternatively, the peptide substrate may have a "branched" primary structure, for example, the ubiquitin moiety is linked to Lys 6 of SEQ ID NO:1 in a peptide substrate comprising the sequence of SEQ ID NO:1 and a ubiquitin moiety, or the ubiquitin moiety is linked to any one or more of Lys 6 and Lys 17 of SEQ ID NO:3 in a peptide substrate comprising the sequence of SEQ ID NO:3 and a ubiquitin moiety. Among the first (N-terminal) 14, 15, or 16 amino acids of any of SEQ ID NOs:1 and 3-15, one or more (e.g., three) residues may be replaced by Ala. In any of SEQ ID NOs:3-15, one or more of the S residues can be replaced by Cys.

In certain embodiments, the 75th amino acid of Ub as represented by the first 76 amino acids of SEQ ID NO:2 may be replaced by Ala. In certain embodiments, the 76th amino acid in SEQ ID NO:2 may be replaced by Ala. The 75th and 76th amino acids may both be replaced by Ala. In preferred embodiments, the 76th amino acid is Gly or Ala, and preferably not Val.

```
SEQ ID NO:1
Met Gln Ile Phe Val Lys Thr Leu Arg Ala Asn Xaa Xaa

Xaa

Xaa can be Ser, Cys, or Ala

SEQ ID NO:2 Ubiquitin (9-coding unit ubiquitin C
(UBC) gene product-the underlined portion is the
76-amino acid single ubiquitin)
>gi|340068|gb|AAA36789.1| ubiquitin
Met Gln Ile Phe Val Lys Thr Leu Thr Gly Lys Thr Ile

Thr Leu Glu Val Glu Pro Ser Asp Thr Ile Glu Asn Val

Lys Ala Lys Ile Gln Asp Lys Glu Gly Ile Pro Pro Asp

Gln Gln Arg Leu Ile Phe Ala Gly Lys Gln Leu Glu Asp

Gly Arg Thr Leu Ser Asp Tyr Asn Ile Gln Lys Glu Ser

Thr Leu His Leu Val Leu Arg Leu Arg Gly Gly Met Gln

Ile Phe Val Lys Thr Leu Thr Gly Lys Thr Ile Thr Leu

Glu Val Glu Pro Ser Asp Thr Ile Glu Asn Val Lys Ala

Lys Ile Gln Asp Lys Glu Gly Ile Pro Pro Asp Gln Gln

Arg Leu Ile Phe Ala Gly Lys Gln Leu Glu Asp Gly Arg

Thr Leu Ser Asp Tyr Asn Ile Gln Lys Glu Ser Thr Leu

His Leu Val Leu Arg Leu Arg Gly Gly Met Gln Ile Phe

Val Lys Thr Leu Thr Gly Lys Thr Ile Thr Leu Glu Val

Glu Pro Ser Asp Thr Ile Glu Asn Val Lys Ala Lys Ile

Gln Asp Lys Glu Gly Ile Pro Pro Asp Gln Gln Arg Leu

Ile Phe Ala Gly Lys Gln Leu Glu Asp Gly Arg Thr Leu

Ser Asp Tyr Asn Ile Gln Lys Glu Ser Thr Leu His Leu

Val Leu Arg Leu Arg Gly Gly Met Gln Ile Phe Val Lys

Thr Leu Thr Gly Lys Thr Ile Thr Leu Glu Val Glu Pro

Ser Asp Thr Ile Glu Asn Val Lys Ala Lys Ile Gln Asp

Lys Glu Gly Ile Pro Pro Asp Gln Gln Arg Leu Ile Phe

Ala Gly Lys Gln Leu Glu Asp Gly Arg Thr Leu Ser Asp

Tyr Asn Ile Gln Lys Glu Ser Thr Leu His Leu Val Leu

Arg Leu Arg Gly Gly Met Gln Ile Phe Val Lys Thr Leu

Thr Gly Lys Thr Ile Thr Leu Glu Val Glu Pro Ser Asp

Thr Ile Glu Asn Val Lys Ala Lys Ile Gln Asp Lys Glu
```

-continued

Gly Ile Pro Pro Asp Gln Gln Arg Leu Ile Phe Ala Gly
Lys Gln Leu Glu Asp Gly Arg Thr Leu Ser Asp Tyr Asn
Ile Gln Lys Glu Ser Thr Leu His Leu Val Leu Arg Leu
Arg Gly Gly Met Gln Ile Phe Val Lys Thr Leu Thr Gly
Lys Thr Ile Thr Leu Glu Val Glu Pro Ser Asp Thr Ile
Glu Asn Val Lys Ala Lys Ile Gln Asp Lys Glu Gly Ile
Pro Pro Asp Gln Gln Arg Leu Ile Phe Ala Gly Lys Gln
Leu Glu Asp Gly Arg Thr Leu Ser Asp Tyr Asn Ile Gln
Lys Glu Ser Thr Leu His Leu Val Leu Arg Leu Arg Gly
Gly Met Gln Ile Phe Val Lys Thr Leu Thr Gly Lys Thr
Ile Thr Leu Glu Val Glu Pro Ser Asp Thr Ile Glu Asn
Val Lys Ala Lys Ile Gln Asp Lys Glu Gly Ile Pro Pro
Asp Gln Gln Arg Leu Ile Phe Ala Gly Lys Gln Leu Glu
Asp Gly Arg Thr Leu Ser Asp Tyr Asn Ile Gln Lys Glu
Ser Thr Leu His Leu Val Leu Arg Leu Arg Gly Gly Met
Gln Ile Phe Val Lys Thr Leu Thr Gly Lys Thr Ile Thr
Leu Glu Val Glu Pro Ser Asp Thr Ile Glu Asn Val Lys
Ala Lys Ile Gln Asp Lys Glu Gly Ile Pro Pro Asp Gln
Gln Arg Leu Ile Phe Ala Gly Lys Gln Leu Glu Asp Gly
Arg Thr Leu Ser Asp Tyr Asn Ile Gln Lys Glu Ser Thr
Leu His Leu Val Leu Arg Leu Arg Gly Gly Met Gln Ile
Phe Val Lys Thr Leu Thr Gly Lys Thr Ile Thr Leu Glu
Val Glu Pro Ser Asp Thr Ile Glu Asn Val Lys Ala Lys
Ile Gln Asp Lys Glu Gly Ile Pro Pro Asp Gln Gln Arg
Leu Ile Phe Ala Gly Lys Gln Leu Glu Asp Gly Arg Thr
Leu Ser Asp Tyr Asn Ile Gln Lys Glu Ser Thr Leu His
Leu Val Leu Arg Leu Arg Gly Gly Val

SEQ ID NO:3 (peptide(29))
Met Gln Ile Phe Val Lys Thr Leu Arg Ala Asn Ser Ser
Ser Val Xaa Lys Leu Ala Ala Ala Leu Yaa His His His
His His His Xaa may be Asp or Ala; Yaa may be Glu or Ala SEQ ID NO:4 (peptide-C14(29))
Met Gln Ile Phe Val Lys Thr Leu Arg Ala Asn Ser Ser
Cys Val Xaa Lys Leu Ala Ala Ala Leu Yaa His His His
His His His Xaa may be Asp or Ala; Yaa may be Glu or Ala SEQ ID NO:5 (peptide-C13(29))
Met Gln Ile Phe Val Lys Thr Leu Arg Ala Asn Ser Cys
Ser Val Xaa Lys Leu Ala Ala Ala Leu Yaa His His His
His His His Xaa may be Asp or Ala; Yaa may be Glu or Ala -continued SEQ ID NO:6 (peptide-C12(29))
Met Gln Ile Phe Val Lys Thr Leu Arg Ala Asn Cys Ser
Ser Val Xaa Lys Leu Ala Ala Ala Leu Yaa His His His
His His His Xaa may be Asp or Ala; Yaa may be Glu or Ala SEQ ID NO:7 (peptide-SΔC(29))
Met Gln Ile Phe Val Lys Thr Leu Arg Ala Asn Cys Cys
Cys Val Xaa Lys Leu Ala Ala Ala Leu Yaa His His His
His His His Xaa may be Asp or Ala; Yaa may be Glu or Ala SEQ ID NO:8 (peptide(28))
Met Gln Ile Phe Val Lys Thr Leu Arg Ala Asn Ser Ser
Ser Val Xaa Lys Leu Ala Ala Ala Leu Yaa His His His
His His Xaa may be Asp or Ala; Yaa may be Glu or Ala SEQ ID NO:9 (peptide(26))
Met Gln Ile Phe Val Lys Thr Leu Arg Ala Asn Ser Ser
Ser Val Xaa Lys Leu Ala Ala Ala Leu Yaa His His His Xaa may be Asp or Ala; Yaa may be Glu or Ala SEQ ID NO:10 (peptide(24))
Met Gln Ile Phe Val Lys Thr Leu Arg Ala Asn Ser Ser
Ser Val Xaa Lys Leu Ala Ala Ala Leu Yaa His Xaa may be Asp or Ala; Yaa may be Glu or Ala SEQ ID NO:11 (peptide(23))
Met Gln Ile Phe Val Lys Thr Leu Arg Ala Asn Ser Ser
Ser Val Xaa Lys Leu Ala Ala Ala Leu Yaa Xaa may be Asp or Ala; Yaa may be Glu or Ala SEQ ID NO:12 (peptide(21))
Met Gln Ile Phe Val Lys Thr Leu Arg Ala Asn Ser Ser
Ser Val Xaa Lys Leu Ala Ala Ala Xaa may be Asp or Ala SEQ ID NO:13 (peptide(18))
Met Gln Ile Phe Val Lys Thr Leu Arg Ala Asn Ser Ser
Ser Val Xaa Lys Leu Xaa may be Asp or Ala SEQ ID NO:14 (peptide(16))
Met Gln Ile Phe Val Lys Thr Leu Arg Ala Asn Ser Ser
Ser Val Xaa Xaa may be Asp or Ala SEQ ID NO:15 (peptide(14))
Met Gln Ile Phe Val Lys Thr Leu Arg Ala Asn Ser Ser
Ser Nucleic acids encoding the various protein and peptide substrates described herein are also provided. The nucleic acids can be useful, e.g., in making the peptide substrates by recombinant molecular biology technology.

In certain embodiments, peptide substrates comprise a detectable agent and/or a target portion that specifically binds or interacts with a selection agent.

By "detectable agent" herein is meant an agent that can be detected and/or "visualized" by methods known in the art. For example, a fluorescent label or a radioactive label can be used as a detectable agent, and a peptide substrate including such a detectable agent can be detected and/or "visualized" by known methods that measure/detect fluorescence (e.g., fluorescence polarization assays) or radioactivity (e.g., autoradiography or scintillation counting). A fluorescent label may comprise a fluorophore or a fluorescent peptide (such as the Green or Blue Fluorescence Protein). Examples of fluorophores include, but are not limited to, FITC, fluorescein-5-maleimide, BODIPY 499/508 maleimide, BODIPY FL N-(2-aminoethyl) maleimide, tetramethylrhodamine-6-maleimide and tetramethylrhodamine-5-maleimide, 5-iodoacetamidofluorescein (5-IAF), 6-iodoacetamidofluorescein (6-IAF), Oregon Green® 488 iodoacetamide, and Oregon Green® 488 maleimide. A fluorophore can be "visualized" in a gel via detection by an anti-fluorophore antibody or in a suitable reaction mixture via detection by a homogeneous fluorescence assay such as fluorescence polarization.

In certain embodiments, a detectable agent is equivalent to a target portion that specifically binds to a selection agent. For example, a fluorescent label with a fluorophore can be a target portion that specifically binds to an anti-fluorophore antibody. In certain embodiments, a detectable agent is distinct from a target portion in that the detectable agent can be directly detected, whereas the target portion further requires a corresponding selection agent to aid in detection and/or visualization. For example, the target portion may be a protein such as GST, and a corresponding selection agent can be an anti-GST antibody which can be used to "visualize" the target portion (and thereby the peptide substrate comprising the target portion) by, for example, ELISA or western blotting. A skilled artisan can appreciate that various molecules, e.g., protein, DNA, RNA, peptidomimetic, small molecule, can serve as the target portion. In preferred embodiments, certain well-known epitopes can be employed as the target portion, e.g., HA tag, FLAG epitope, Myc epitope, His6 tag, and T7 epitope, and their corresponding, well-known antibodies can be employed to determine their presence or absence. For a target portion such as the His6 tag, a divalent metal ion (e.g., $Ni^{2+}$) can also serve as a selection agent.

In certain preferred embodiments, a target portion is located at the N-terminus of a peptide substrate of the application.

Methods of Making the Peptides

The present application further provides methods of making the peptide substrates described herein.

In certain embodiments, the peptides, e.g., any of SEQ ID NOs:1 and 3-15 can be manufactured by standard chemical peptide synthesis. Alternatively, recombinant, molecular biology techniques can be used. In certain embodiments, chemical synthesis and recombinant technology may be employed in combination to make the peptide substrates of the application.

A nucleic acid encoding a protein of the application may comprise a fusion gene or nucleic acid (e.g., a fusion nucleic acid encoding a peptide substrate comprising a ubiquitin moiety "fused" with a sequence of any of SEQ ID NOs:1 and 3-15), methods of making which are known in the art. For example, the joining of various DNA or gene fragments (e.g., a DNA fragment comprising a nucleic acid encoding a ubiquitin moiety, and a DNA fragment comprising a nucleic acid encoding a peptide having the sequence of any of SEQ ID NOs:1 and 3-15) coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In certain embodiments, PCR amplification of gene fragments can be carried out using anchor primers which give rise to complementary overhangs between two consecutive gene fragments which can subsequently be annealed to generate a fusion or chimeric gene sequence (see, for example, Current Protocols in Molecular Biology, eds. Ausubel et al., John Wiley & Sons: 1992).

The recombinant nucleic acid constructs of the disclosure can be manufactured by using conventional recombinant DNA methodologies well known and thoroughly documented in the art, as well as by using well-known biosynthetic and chemosynthetic methodologies using routine peptide or nucleotide chemistries and automated peptide or nucleotide synthesizers. Such routine methodologies are described for example in the following publications, the teachings of which are incorporated by reference herein: Hilvert, 1 Chem.-Biol. 201-3 (1994); Muir et al., 95 Proc. Natl. Acad. Sci. USA 6705-10 (1998); Wallace, 6 Cuff. Opin. Biotechnol. 40310 (1995); Miranda et al., 96 Proc. Natl. Acad. Sci. USA 1181-86 (1999); Liu et al., 91 Proc. Natl. Acad. Sci. USA 6584-88 (1994). Suitable for use in the present disclosure are naturally-occurring amino acids and nucleotides; non-naturally occurring amino acids and nucleotides; modified or unusual amino acids; modified bases; amino acid sequences that contain post-translationally modified amino acids and/or modified linkages, cross-links and end caps, non-peptidyl bonds, etc.; and, further including without limitation, those moieties disclosed in the World Intellectual Documentation. Standard St. 25 (1998) including Tables 1 through 6 in Appendix 2, herein incorporated by reference. Equivalents of the foregoing will be appreciated by the skilled artisan relying only on routine experimentation together with the knowledge of the art.

For example, the contemplated DNA constructs may be manufactured by the assembly of synthetic nucleotide sequences and/or joining DNA restriction fragments to produce a synthetic DNA molecule. The DNA molecules then are ligated, cloned or subcloned into an expression vehicle, for example an expression plasmid (e.g., pET28a or pGEX), and transfected into an appropriate host cell, for example *E. coli*. The contemplated protein construct encoded by the DNA molecule then is expressed, purified, refolded, tested in vitro for certain attributes, e.g., binding activity with a selection agent (e.g., an anti-Myc antibody) having binding affinity for its corresponding target portion (e.g., the Myc epitope) in the peptide substrates, and/or ability to serve as an enzymatic substrate for measuring proteasome activity.

Methods of Using the Peptides for Selecting Agents that Modulate Proteasome Activity The present application also provides methods of using the peptide substrates described herein, e.g., in selecting one or more agents that modulate proteasome activity. As described above, proteasome activity involves various components, and an agent can be selected that modulates a particular component of proteasome activity, e.g., the entry of a protein targeted for degradation (e.g., modified by ubiquitination) into proteasome, Rpn11 or another metalloprotease activity of the 19S regulatory particle, the ATPase activity, or core peptidase activity of the 20S complex.

In one embodiment, an enzyme or enzymatic preparation used in the screening assays provided by the present application is a polypeptide complex of 26S proteasome or 19S regulatory particle, or a polypeptide or polypeptide complex having Rpn11 enzymatic activity. A polypeptide complex of the 26S proteasome or the 19S regulatory particle, or a polypeptide or polypeptide complex having Rpn11 enzymatic activity can be obtained by any suitable methodology. For example, 26S proteasome can be purified from eukaryotic cells or tissues, e.g., S. cerevisiae or human.

In another embodiment, the incubation in the presence and absence of a test agent, a target protein or peptide substrate, and 26S proteasome of the screening assays provided by the present application is optionally carried out in the presence of a 20S proteasome inhibitor. Any 20S proteasome inhibitor or inhibitor of the degradation process can be used for the purpose of the present application. For example, a 20S proteasome inhibitor can be MG132, lactacystin, epoxomycin, YU101, PS-349, PS-519, LLnL, or the derivatives thereof. In general, such inhibitor prevents or decreases the degradation of a target protein that is not conjugated to ubiquitin.

In yet another embodiment, the incubation is conducted further in the presence of an energy source, e.g., ATP. In still another embodiment, the incubation is conducted further in the presence of an inhibitor of deubiquitination by a conventional ubiquitin isopeptidase, e.g., a ubiquitin isopeptidase other than those that associated with a JAB subunit such as 26S proteasome. One example of such inhibitor is ubiquitin aldehyde, e.g., at 2-5 μM.

In certain embodiments, detecting proteasome enzymatic activity employs a ubiquitinated protein substrate such as a peptide substrate as described herein, and the reaction was monitored by SDS-PAGE followed by immunoblotting with either anti-ubiquitin antibody or another antibody specific to another component of the peptide substrate, e.g., a target portion such as Myc. Alternatively, after being exposed to the enzyme or enzymatic preparation to be tested, the peptide substrates that comprise a radio- or fluorescent-label can be subject to SDS-PAGE to separate the uncleaved peptide substrate from the cleaved product (Eytan et al., supra) or TCA-precipitation (Yao et al., Nature 419: 403-407 (2002)), and the radioactivity or fluorescence can be detected with known means in the art.

Certain embodiments provide a method for selecting an agent that modulates proteasome activity, for example, enzymatic activity of the 26S proteasome, the 19S regulatory particle, or a polypeptide or polypeptide complex having Rpn11 enzymatic activity. The method may include providing a peptide substrate of the application, for example, a peptide substrate comprising an amino acid sequence of SEQ ID NO:1 and one or more ubiquitin moieties, and combining the peptide with a reaction mixture suitable for measuring proteasome activity in the presence of a test agent. A change in the proteasome activity in the presence of the test agent as compared to the proteasome activity in the absence of the test agent indicates that the test agent modulates the proteasome activity. The proteasome activity can be determined by, for example, measuring the level of cleavage of the ubiquitin moiety(s) from the peptide. The level of cleavage may be indicated by the rate and/or extent of cleavage. The method is useful for selecting an agent that enhances or inhibits the proteasome activity.

A recent publication (Verma et al., Science 306: 117-120 (2004)) identified another type of proteasome inhibitor, termed "Ubistatin." Ubistatin functions via binding to the ubiquitin or polyubiquitin chains linked to the protein targeted for degradation, and thereby preventing the peptide molecule from entering the proteasome. Peptide substrates of the present application can be employed to screen for ubistatin-like proteasome inhibitors. For example, a peptide substrate of the application can be used to compare a test inhibitor agent's effect on 26S proteasome activity (e.g., by measuring $IC_{50}$) to its effect on Isopeptidase T activity. If the effects are equivalent for the different enzymes or enzyme preparations, the test inhibitor agent is acting on the peptide substrate, not on the enzymes, and thus acts like a ubistatin molecule. It is also noted that Ubistatin A, also referred to as Compound 92 (Verma et al., 2004, supra), binds to a protein substrate, and the intrinsic fluorescence detected from Compound 92 increases. This inherent characteristic therefore allows one to screen for ubistatin-like molecules in an assay that measures changes, in the presence as compared to in the absence of a test agent, in intrinsic fluorescence of ubistatin and/or the test agent. A competition-based assay may be used where a ubistatin molecule, a test agent, and a peptide substrate are combined together in a suitable assay/reaction mixture for measuring intrinsic fluorescence, and a change in the intrinsic fluorescence of ubistatin in the presence as compared to the absence of the test agent in the mixture indicates that the test agent may be ubistatin-like and may compete against ubistatin for binding to the peptide substrate. Another assay may be employed where a test agent and a peptide substrate are combined together in a suitable assay/reaction mixture for measuring intrinsic fluorescence, and a change in the intrinsic fluorescence of the test agent in the presence of the peptide substrate indicates that the test agent is a ubistatin-like proteasome inhibitor.

A screening method of the application may include providing a peptide substrate of the application that has a fluorescent label, e.g., a peptide substrate comprising an amino acid sequence of SEQ ID NO:1, one or more ubiquitin moieties, and a fluorescent label, and determining the fluorescence polarization of the peptide substrate in the presence as compared to the absence of a test agent. A difference in the fluorescence polarization in the presence of the test agent versus in the absence of the test agent indicates that the test agent may be a proteasome inhibitor agent. While not wishing to be bound by any theory, the test agent may function in a ubistatin-like manner, for example, causing aggregation or multimerization of ubiquitin moieties of the peptide substrates. Such aggregation or multimerization can be detected by any methodology suitable for detecting changes in molecular weight and/or size of molecules, for example, the peptide substrates. A suitable methodology can be native gel-electrophoresis, size-exclusion (or gel filtration) chromatography, fluorescence polarization, light scattering, or any other suitable means.

Certain embodiments provide a method for selecting a proteasome inhibitor agent. The proteasome inhibitor agent may comprise a ubistatin-like molecule or a ubiquitin-binding molecule. The proteasome inhibitor agent that binds ubiquitin may inhibit the substrate from being proteolyzed or may inhibit proteasome activity through other mechanisms. The inhibitor agent may or may not have intrinsic fluorescence.

Certain embodiments also provide a method for selecting a proteasome inhibitor agent that modulates the AAA ATPase activity. While not wishing to be bound by any particular theory, it has been noted that the AAA ATPase activity is coupled with the Rpn11 enzymatic activity. Accordingly, an inhibitor agent specific to the Rpn11 enzymatic activity may also modulate the AAA ATPase activity.

A further aspect of the application provides a method for selecting an agent that modulates activity of various components of proteasome or various stages of the ubiquitin-mediated proteolysis process. The various components of proteasome and various stages of the ubiquitin-mediated proteolysis may include entry into the proteasome of ubiquitinated proteins; deubiquitination of the proteins, e.g., by Rpn11; unfolding of the proteins, e.g., AAA ATPase; degradation of the deubiquitinated proteins by a core peptidase.

The method may employ at least two peptide substrates, for example, a first peptide substrate comprising a ubiquitinated-peptide and a first fluorescent label, and a second peptide substrate comprising a non-ubiquitinated peptide and a second fluorescent label, wherein the first and second fluorescent labels are detectable at different wavelengths. A ubiquitinated-peptide may comprise an amino acid sequence of SEQ ID NO:1 and ubiquitin moieties. A non-ubiquitinated peptide may be any peptide that can serve as a substrate for a core peptidase, e.g., a chymotryptic-like protease, a tryptic-like protease, or a PGPH (or caspase)-like protease. The method may also include measuring the fluorescence at the first label detectable wavelength in the presence and absence of a test agent, and optionally also measuring the fluorescence at the second label detectable wavelength in the presence and absence of a test agent. A change in fluorescence of the first peptide substrate in the presence of the test agent as compared to the fluorescence in the absence of the test agent indicates that the test agent modulates an activity associated with the 19S regulatory particle. A change in fluorescence of the second peptide substrate in the presence of the test agent as compared to the fluorescence in the absence of the test agent indicates that the test agent modulates a 20S core peptidase.

The application further provides high-throughput assays employing certain peptide substrates (e.g., a peptide substrate comprising a fluorescent label) described herein, which assays can be designed based on the methods described herein. The high-throughput assays are particularly useful for selecting and identifying agents that can modulate proteasome activity and thereby ubiquitin-mediated protein degradation.

In preferred embodiments, a high-throughput assay of the application employs a screening method that determines whether a test agent causes size and/or molecular weight changes of a peptide substrate in a suitable reaction mixture. Such screening method may employ a fluorescence polarization assay to measure changes in size and/or molecular weight of the peptide substrate.

The test agent used for the screening methods of the present application can be any agent from any library of compounds or molecules. In one embodiment, the test agent is selected or derived from compounds likely to inhibit the activity of metalloproteinase, e.g., compounds having zinc-binding functionality. For example, the test agent can be any compounds having a hydroxamate moiety or a member of a hydroxamate compound library, reverse hydroxamate compound library, thiol compound library, carboxylate compound library, or phosphonic acid compound library.

Agents tested in the methods of screening for or identifying agents that modulate proteasome activity provided herein can be of any physical type. Examples of agents include, but are not limited to, biomolecules, including, but not limited to, amino acids, peptides, polypeptides, peptidomimetics, nucleotides, nucleic acids (including DNA, cDNA, RNA, antisense RNA and any double- or single-stranded forms of nucleic acids and derivatives and structural analogs thereof), polynucleotides, saccharides, fatty acids, steroids, carbohydrates, lipids, lipoproteins and glycoproteins. Such bioniolecules can be substantially purified, or can be present in a mixture, such as a cell extract or supernatant. Test agents further include synthetic or natural chemical compounds, such as simple or complex organic molecules, metal-containing compounds and inorganic ions (including, for example, $Gd^{3+}$, lead and lanthanum). Also included are pharmacological compounds, which optionally can be subjected to directed or random chemical modifications, such as acylation, alkylation, esterification, amidation, etc., to produce structural analogs.

Uses of Selected Agents

Another aspect of the application provides methods and compositions employing an agent selected according a method of the application. For example, certain embodiments provide a method for treating or preventing in a subject a condition associated with ubiquitin-mediated proteolysis or proteasome activity comprising administering to the subject a composition comprising an agent that modulates the proteasome activity, particularly, the Rpn11 enzymatic activity.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

According to this aspect of the present application, any agent that is capable of inhibiting or decreasing the proteasome activity, e.g., by modulating deconjugation, removal, or separation of a ubiquitin molecule from a target protein can be used prophylactically or therapeutically to treat or to prevent various conditions associated with protein regulation by degradation or proteolysis. For example, any agent identified by the screening methods of the present application that is able to decrease the deconjugation of a ubiquitin from a target protein, e.g., an inhibitor of the isopeptidase activity of 26S proteasome can be used therapeutically to treat neoplastic growth, angiogenesis, infection, inflammation, immune-related diseases, ischemia and reperfusion injury, multiple sclerosis, rheumatoid arthritis, neurodegenerative conditions, and psoriasis. Certain condition or disorder associated with aberrant ubiquitin-mediated protein degradation or proteasome activity may be characterized by the accumulation of ubiquitinated proteins.

Many diseases and conditions are associated with protein regulation by proteolysis or proteasome activity. Such diseases and conditions include restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation. Agents identified or selected by the present application may be useful for the treatment of conditions associated with chronic inflammation, including, but not limited to COPD, psoriasis, bronchitis, emphysema, and cystic fibrosis.

The agents identified herein can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins, TGF-β, and transcription factor NF-κB.

Another embodiment of the application is the use of the agents identified herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., Fed. Eur. Biochem. Soc., (1992) 304: 57-60). The APP-processing enzyme cleaves at the Gln 15—Lys 16 bond; in the presence of calcium ion, the enzyme also cleaves at the Met-1—Asp1 bond, and the Asp1—Ala2 bonds to release the extracellular domain of β-AP.

One embodiment, therefore, is a method of treating Alzheimer's disease, including administering to a subject an effective amount of an agent or composition (e.g., pharmaceutical composition) disclosed herein. Such treatment includes reducing the rate of β-AP processing, reducing the rate of β-AP plaque formation, reducing the rate of β-AP generation, and reducing the clinical signs of Alzheimer's disease.

Other embodiments of the application relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Inhibitor agents of the application are useful for treating conditions such as cancer, chronic infectious diseases, fever, muscle disuse (atrophy) and denervation, nerve injury, fasting, renal failure associated with acidosis, diabetes, and hepatic failure. See, e.g., U.S. Pat. No. 5,340,736. Embodiments of the application therefore encompass methods for: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of an agent or composition (e.g., pharmaceutical composition) disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity. However, accelerated degradation of the TGF-β signaling components has been observed in cancers and other hyperproliferative conditions. Thus, certain embodiments of the application relate to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, an additional embodiment of the application is the topical or systemic administration of the inhibitors to treat burns. Wound closure following surgery is often associated with disfiguring scars, which may be prevented by inhibition of fibrosis. Thus, in certain embodiments, the application relates to a method for the prevention or reduction of scarring.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β(Palombella et al., Cell (1994) 78:773-785). Some embodiments of the application include methods of affecting the level of expression of IL-2, MHC-I, IL-6, TNFα, IFN-βor any of the other previously-mentioned proteins, each method including administering to a subject an effective amount of an agent identified herein. Complexes including p50are rapid mediators of acute inflammatory and immune responses (Thanos, D. and Maniatis, T., Cell (1995) 80:529-532).

NF-κB also participates in the expression of the cell adhesion genes that encode E-selectin, P-selectin, ICAM, and VCAM-1 (Collins, T., Lab. Invest. (1993) 68:499-508). One embodiment of the application is a method for inhibiting cell adhesion (e.g., cell adhesion mediated by E-selectin, P-selectin, ICAM, or VCAM-1), including contacting a cell with (or administering to a subject) an effective amount of an agent (or a pharmaceutical composition) identified herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Therefore, certain embodiments of the application relate to a method of treating an ischemic condition or reperfusion injury comprising administering to a subject in need of such treatment an effective amount of an agent identified herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, (1995) 267:960). Two embodiments of the application are a method for inhibiting or reducing HIV infection in a subject, and a method for decreasing the level of viral gene expression, each method including administering to the subject an effective amount of an agent identified herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., J. Immun. (2003) 171: 1515-1525). Therefore, in certain embodiments, agents identified in the application may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to an agent described herein. An agent of the application may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for suppressing the immune system of a subject (e.g., inhibiting transplant rejection, allergies, auto-immune diseases, and asthma), including administering to the subject an effective amount of an agent identified herein.

Another further embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. Cell (1994) 78:773-785; and Traenckner, et al., EMBO J. (1994) 13:5433-5441). One embodiment of the application is a method for inhibiting IκB-α degradation, including contacting the cell with an agent identified herein. A further embodiment is a method for reducing the cellular content of NF-κB in a cell, muscle, organ, or subject, including contacting the cell, muscle, organ, or subject with an agent identified herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the application are methods for affecting cyclin-dependent eukaryotic cell cycles, including exposing a cell (in vitro or in vivo) to an agent identified herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with $p34^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). One embodiment of the application is a method for treating a proliferative disease in a subject (e.g., cancer, psoriasis, or restenosis), including administering to the subject an effective amount of an agent identified herein. The application also encompasses a method for treating cyclin-related inflammation in a subject, including administering to a subject a therapeutically effective amount of an agent identified herein.

Additional embodiments are methods for affecting the proteasome-dependent regulation of oncoproteins and methods of treating or inhibiting cancer growth, each method including exposing a cell (in vivo, e.g., in a subject, or in vitro) to an agent identified herein. HPV-16 and HPV-18-derived E6 proteins stimulate ATP-and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of an agent identified herein.

In another embodiment, the agents of the present application are useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, entamoeba species have been shown to lose encystation capacity when exposed to proteasome inhibitors (Gonzales, et al., Arch. Med. Res. 1997, 28, Spec No: 139-140). In certain such embodiments, the agents are useful for the treatment of parasitic infections in humans caused by a protozoan parasite selected from Plasmodium sps. (including P. falciparum, P. vivax, P. malariae, and P. ovale, which cause malaria), Trypanosoma sps. (including T. cruzi, which causes Chagas' disease, and T. brucei which causes African sleeping sickness), Leishmania sps. (including L. amazonensis, L. donovani, L. infantum, L. mexicana, etc.), Pneumocystis carinii (a protozoan known to cause pneumonia in AIDS and other immunosuppressed patients), Toxoplasma gondii, Entamoeba histolytica, Entamoeba invadens, and Giardia lamblia. In certain embodiments, the agents are useful for the treatment of parasitic infections in animals and livestock caused by a protozoan parasite selected from Plasmodium hermani, Cryptosporidium sps., Echinococcus granulosus, Eimeria tenella, Sarcocystis neurona, and Neurospora crassa. Other compounds useful as proteasome inhibitors in the treatment of parasitic diseases are described in WO 98/10779, which is incorporated herein in its entirety.

In certain embodiments, the inhibitor agents inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., J. Clin. Invest. (2003) 111: 1771-1782), therefore suggesting that the ubiquitin-proteasome machinery regulates osteoblast differentiation and bone formation. Therefore, the inhibitor agents identified herein may be useful in the treatment and/or prevention of diseases associated with bone loss, such as osteroporosis.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., Trans Genet (1992) 8:55-61 describes evidence that bone morphogenetic proteins (BMPs), are differentially expressed in hair follicles during development. Harris, S. E., et al., J Bone Miner Res (1994) 9:855-863 describes the effects of TGFβ on expression of BMP-2 and other substances in bone cells. BMP-2 expression in mature follicles also occurs during maturation and after the period of cell proliferation (Hardy, et al., supra). Thus, agents of the application may also be useful for hair follicle growth stimulation.

The agents identified herein can also be useful as diagnostic agents (e.g., in diagnostic kits or for use in clinical laboratories) for screening for proteins (e.g., enzymes, transcription factors) processed by Ntn hydrolases, including the proteasome. The agents are also useful as research reagents for specifically binding the X/MB 1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Inhibitors identified herein can be used to determine whether a cellular, developmental, or physiological process or output is regulated by proteolytic activity. One such method includes obtaining an organism, an intact cell preparation, or a cell extract; exposing the organism, cell preparation, or cell extract to an agent identified herein; exposing the agent-exposed organism, cell preparation, or cell extract to a signal, and monitoring the process or output.

The agents of the present application useful for therapeutic treatment can be administered alone, in a composition with a suitable pharmaceutical carrier, or in combination with other therapeutic agents. An effective amount of the agents to be administered can be determined on a case-by-case basis. Factors to be considered usually include age, body weight, stage of the condition, other disease conditions, duration of the treatment, and the response to the initial treatment. Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art. The agents of the present application may be administered in any way which is medically acceptable which may depend on the identity of the agent and/or on the disease condition or injury being treated. Possible administration routes include injections, parenteral routes such as intravascular, intravenous, intraepidural or others, as well as oral, nasal, ophthalmic, rectal, topical, or pulmonary, e.g., by inhalation, aerosolization or nebulization. The agents may also be directly applied to tissue surfaces, e.g., during surgery. Sustained release administration is also specifically included in the application, by such means as depot injections or erodible implants. Examples of diseases and conditions that are subject to a treatment using drug coated medical devices that release compounds identified using the methods of the present application include atherosclerosis, acute coronary syndrome, Alzheimer's disease, cancer, fever, muscle disuse (atrophy), denervation, vascular occlusions, stroke, HIV infection, nerve injury, renal failure associated with acidosis, and hepatic failure. See, e.g., U.S. Pat. No. 5,340,736.

EXAMPLES

Example 1

Reagents

1) Buffer A (50 mM Tris pH 7.4, 0.01% NP-40, 1 mM DTT; 7.5 μM MgC12; 7.5 μM ATP);

2) Ub4-pep-C14(29)-Oregon Green prepared using Ub4-pep-C14(29) covalently coupled to Oregon Green 488 iodoacetamide and purified away from the starting product;

3) LLVY-AMC, purchased from Boston Biochem;

4) 26S proteasome purified from humans and purchased from BioMol;

5) 384 well polystyrene plates purchased from Molecular Devices;

6) Ubistatin A (Compound 92 or C92); 7) isopeptidase T from rabbit purchased from Boston Biochem

Example 2

Method

5 μl of compound [30 μM compound in Buffer A+1% DMSO], 5 μl of substrate [30 nM Ub4-pep-C14(29)-Oregon Green and 15 μM LLVY-AMC in Buffer A] and 5 μl enzyme [1.5 nM 26S proteasomes] were mixed in a 384 well plates and incubated at 28° C. for 75 minutes. Reactions were stopped with the addition of 5 μl 4 μM 20S inhibitor (PR-171) and 4 mM EDTA. Processing of the 20S substrate LLVY-AMC to liberate AMC was determined by measuring the AMC fluorescence [excitation at 340 nm; emission at 465 nm]. Processing of the 19S substrate Ub4-pep-C14(29)-Oregon Green to liberate pep-C14(29)-Oregon Green was determined by measuring the fluorescence polarization of Oregon Green [excitation at 485 nm; emission at 535 nm].

Example 3

Different Categories of Modulators or Test Agents

Modulators of the 20S proteasome activity affect liberation of AMC from LLVY-AMC (second non-ubiquitinated substrate) and affect the chymotryptic-like activity of the 20S proteasome.

Modulators of the 19S proteasome activity affect liberation of pep-C14(29)-Oregon Green from Ub4-pep-C14(29)-Oregon Green (first ubiquitinated substrate). These modulators may act in one of three ways:

1) Binding to ubiquitin thereby preventing the substrate Ub4-pep-C14(29)-Oregon Green from being processed by the 19S proteasome.

2) Inhibiting the AAA ATPase activity of the 19S proteasome.

3) Inhibiting the Rpn11 isopeptidase activity of the 19S proteasome.

Example 4

Binding of a Test Agent to Ubiquitin Can Be Ascertained By One or Several of the Following Assays 1) The $IC_{50}$ for a test agent's action on processing the substrate Ub4-pep-C 14(29)-Oregon Green by the enzyme 26S proteasome is equivalent to the $IC_{50}$ for a test agent's action on processing the substrate Ub4-pep-C14(29)-Oregon Green by an unrelated deubiquitinating enzyme(e.g., isopeptidase T). The test agent is acting on the substrate Ub4-pep-C14(29)-Oregon Green and preventing its processing by deubiquitinating enzymes.

2) The test agent acts to multimerize Ub4-pep-C14(29)-Oregon Green thereby preventing liberation of the pep-C14(29)-Oregon Green. Multimerization can be detected by one of several methods e.g. gel-filtration; light-scattering; native-gel electrophoresis; fluorescence polarization.

3) The intrinsic fluorescence of a test agent either increases or decreases upon binding to Ub4-pep-C14(29), where the test agent has an intrinsic fluorescence.

4) When 2.5 μM of ubistatin A (C92) is incubated with 2.5 μM of Ub4-pep-C14(29), the intrinsic fluorescence of ubistatin A (C92) [excitation at 350 nm; emission at 450 nm] increases several fold. A test agent that binds ubiquitin can affect the binding of ubistatin A (C92) to Ub4-pep-C14(29). This can be determined by measuring the intrinsic fluorescence of ubistatin A (C92) [excitation at 350 nm; emission at 450 nm] with Ub4-pep-C14(29) in the presence or absence of a test agent, which is a competition assay between ubistatin A and the test agent for binding to the ubiquitin.

Example 5

Inhibition of the AAA ATPase Activity of the 19S Proteasome by a Test Agent Can be Ascertained by One or Both of the Following Assays 1) The $IC_{50}$ for a test agent's action on processing the substrate Ub4-pep-C14(29)-Oregon Green by the enzyme 26S proteasome in Buffer A is lower compared to the $IC_{50}$ for a test agent's action on processing the substrate Ub4-pep-C14(29)-Oregon Green by the enzyme 26S proteasome in Buffer A with 750 mM ATP and 750 mM $MgCl_2$. The action of such a test agent would be competitive with ATP and thereby occupying the ATP sites in the AAA ATPase.

2) The test agent affects the liberation of phosphate from ATP by the 26S proteasome. Phosphate levels can be determined by standard methods, for example, a malachite green binding assay.

Example 6

Inhibition of the Rpn11 Activity of the 19S Proteasome by a Test Agent

The assay can be designed based on the fact that the test agent affects liberation of pep-C14(29)-Oregon Green from Ub4-pep-C14(29)-Oregon Green but does not fall into the categories of inhibitor agents identified by Examples 4 and 5 as described above.

Example 7

Compounds Identified as Inhibitors

Using the method described in Example 2, the following compounds were identified as inhibitors of 26S proteasome activity:

Compound 1

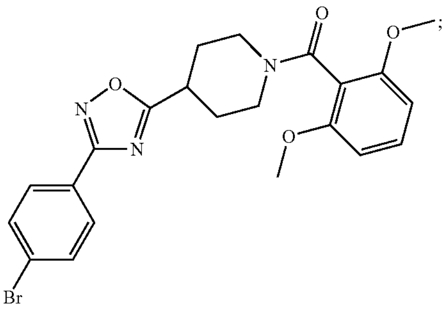

Compound 2

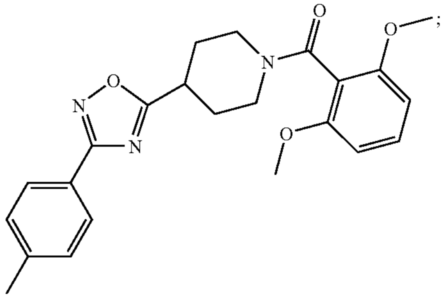

Compound 3

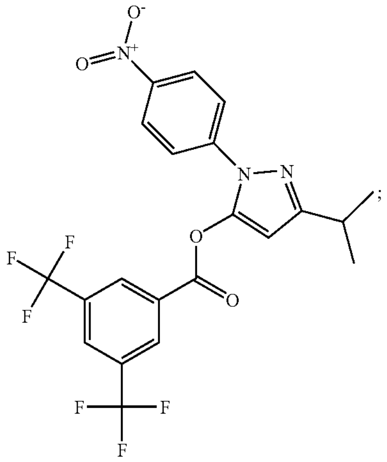

and

-continued

Compound 4

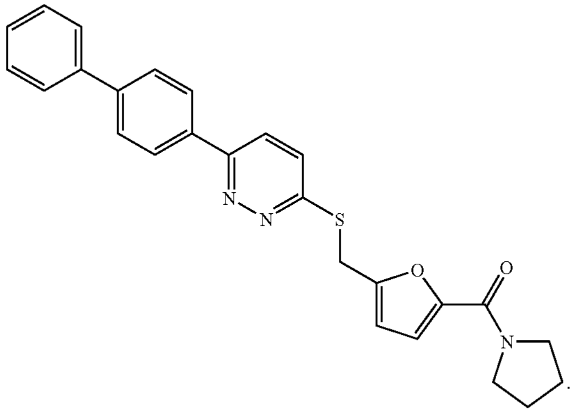

The molecules can further be categorized based on which substrate was perturbed, as described in Example 3. Compounds 1, 2 and 3 affect the chymotryptic-like activity of the 20S proteasome. Compound 4 prevents the substrate Ub4-pep-C14(29)-Oregon Green from being processed by the 19S proteasome.

It should be recognized that these compounds may be useful for any application disclosed herein.

References

All publications and patents mentioned herein, are hereby incorporated by reference in their entirety as if each individual publication or patent was specifically and individually indicated to be incorporated by reference.

Equivalents

Those skilled in the art will recognize, or be able to ascertain using no more than routine experimentation, many equivalents to the specific embodiments of the application described herein. Such equivalents are intended to be encompassed by the following claims.

We claim:

1. An isolated peptide comprising an amino acid sequence at least 80% identical to SEQ ID NO:1 and at least one ubiquitin moiety that is at least 90% identical to the first 76-amino acid sequence of SEQ ID NO:2, wherein a deubiquitinating protease deubiquitinates the peptide.

2. The peptide of claim 1, wherein the protease is a deubiquitinating metalloprotease.

3. The peptide of claim 1, wherein the protease is a deubiquitinating non-metalloprotease.

4. The peptide of claim 1, wherein the protease is Rpn11.

5. The peptide of claim 1, further comprising at least 3 additional amino acids at the C-terminus of the peptide.

6. The peptide of claim 1, wherein the amino acid sequence has the amino acid sequence of SEQ ID NO:1 wherein at least one non-Ala amino acid is replaced by Ala.

7. The peptide of claim 1, wherein the amino acid sequence has the amino acid sequence of SEQ ID NO:4 wherein at least one non-Ala amino acid is replaced by Ala.

8. The peptide of claim 1, further comprising one or more ubiquitin moieties at the N-terminus of the peptide.

9. The peptide of claim 8, wherein the ubiquitin moiety consists of two or more repeats of an amino acid sequence that is at least 90% identical to the first 76-amino acid sequence of SEQ ID NO:2.

10. The peptide of claim 1, wherein the ubiquitin moiety comprises the first 76-amino acid sequence of SEQ ID NO:2 modified such that the 75th amino acid is an Ala.

11. The peptide of claim 1, wherein the ubiquitin moiety comprises the first 76-amino acid sequence of SEQ ID NO:2 modified such that the 76th amino acid is an Ala.

12. The peptide of claim 1, further comprising a detectable agent linked to the peptide.

13. The peptide of claim 12, wherein the detectable agent is a fluorescent label.

14. The peptide of claim 13, wherein the fluorescent label is a fluorescent peptide linked to the C-terminus of the peptide by a peptide bond.

15. The peptide of claim 12, wherein the detectable agent is a radioactive label.

16. The peptide of claim 1 further comprising an N-terminal target portion or C-terminal target portion that specifically binds to a selection agent.

17. The peptide of claim 16, wherein the selection agent is an antibody.

18. The peptide of claim 16, wherein the selection agent is a divalent metal ion.

19. The peptide of claim 1, wherein the peptide comprises SEQ ID NO: 1 and at least one ubiquitin moiety that is at least 90% identical to the first 76-amino acid sequence of SEQ ID NO:2.

20. The peptide of claim 19, wherein the peptide comprises SEQ ID NO: 1 and at least one ubiquitin moiety that is identical to the first 76-amino acid sequence of SEQ ID NO:2.

21. The peptide of claim 1, wherein the peptide comprises at least one of the amino acid sequences as set forth in SEQ ID NOs: 3-15 and at least one ubiquitin moiety that is at least 90% identical to the first 76-amino acid sequence of SEQ ID NO:2.

22. The peptide of claim 21, wherein the peptide comprises at least one of the amino acid sequences as set forth in SEQ ID NOs: 3-15 and at least one ubiquitin moiety that is identical to the first 76-amino acid sequence of SEQ ID NO:2.

23. The peptide of claim 10, wherein the peptide comprises SEQ ID NO: 1.

24. The peptide of claim 11, wherein the peptide comprises SEQ ID NO: 1.

25. The peptide of claim 10, wherein the peptide comprises at least one of the amino acid sequences as set forth in SEQ ID NOs: 3-15.

26. The peptide of claim 11, wherein the peptide comprises at least one of the amino acid sequences as set forth in SEQ ID NOs: 3-15.

27. The peptide of claim 1, wherein the deubiquitinating protease comprises a JAMM motif.

28. The peptide of claim 27, wherein the JAMM motif comprises the amino acid sequence of SEQ ID NO: 17 or SEQ ID NO:18.

* * * * *